(12) United States Patent
Godo

(10) Patent No.: US 11,134,831 B2
(45) Date of Patent: Oct. 5, 2021

(54) CAPSULE ENDOSCOPE HAVING IMAGING SYNCHRONIZATION BASED ON DATA FROM AN IMAGE SENSOR AND ANOTHER SENSOR

(71) Applicant: OLYMPUS CORPORATION, Tokyo (JP)

(72) Inventor: Hirokazu Godo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 445 days.

(21) Appl. No.: 16/040,605

(22) Filed: Jul. 20, 2018

(65) Prior Publication Data

US 2018/0325363 A1 Nov. 15, 2018

Related U.S. Application Data

(63) Continuation of application No. PCT/JP2016/051966, filed on Jan. 25, 2016.

(51) Int. Cl.
*A61B 1/04* (2006.01)
*A61B 1/00* (2006.01)
*A61B 1/045* (2006.01)

(52) U.S. Cl.
CPC .......... *A61B 1/041* (2013.01); *A61B 1/0002* (2013.01); *A61B 1/00006* (2013.01);
(Continued)

(58) Field of Classification Search
None
See application file for complete search history.

(56) References Cited

U.S. PATENT DOCUMENTS 6,709,387 B1 3/2004 Glukhovsky et al.
2004/0073087 A1* 4/2004 Glukhovsky ...... A61B 1/00158
600/109
(Continued)

FOREIGN PATENT DOCUMENTS

EP 2000077 A1 12/2008
JP 2004-154176 A 6/2004
(Continued)

OTHER PUBLICATIONS

International Search Report dated Apr. 26, 2016 issued in PCT/JP2016/051966.
(Continued)

*Primary Examiner* — John P Leubecker
(74) *Attorney, Agent, or Firm* — Scully, Scott, Murphy & Presser, P.C.

(57) ABSTRACT

A capsule endoscope includes a first sensor, a second sensor, an information generator, a signal generator, and an imager. The information generator generates third instruction information on the basis of the first instruction information and the second instruction information. The first instruction information is an analysis result of first data generated by the first sensor. The second instruction information is an analysis result of second data generated by the second sensor. The signal generator generates an imaging synchronization signal on the basis of the third instruction information. The imager performs imaging on the basis of the imaging synchronization signal and acquires an image. The information generator generates the third instruction information on the basis of a combination of at least three pieces of instruction information.

16 Claims, 10 Drawing Sheets

(52) U.S. Cl.
    CPC ...... *A61B 1/00009* (2013.01); *A61B 1/00016* (2013.01); *A61B 1/045* (2013.01)

(56) References Cited

U.S. PATENT DOCUMENTS

| | | | |
|---|---|---|---|
| 2008/0242931 | A1 | 10/2008 | Nishino |
| 2009/0240108 | A1* | 9/2009 | Shimizu ................ A61B 1/041 600/109 |
| 2009/0322865 | A1* | 12/2009 | Wang ................ A61B 5/14539 348/68 |
| 2012/0271104 | A1* | 10/2012 | Khait .................... A61B 1/041 600/109 |
| 2015/0297067 | A1* | 10/2015 | Yanagidate ............. A61B 5/06 600/109 |
| 2017/0020374 | A1* | 1/2017 | Duan ................ A61B 1/00036 |

FOREIGN PATENT DOCUMENTS

| | | |
|---|---|---|
| JP | 2006-223892 A | 8/2006 |
| JP | 2008-237639 A | 10/2008 |
| JP | 2009-195271 A | 9/2009 |
| JP | 2010-035746 A | 2/2010 |
| JP | 2010-524557 A | 7/2010 |
| JP | 2012-071186 A | 4/2012 |
| JP | 2015-077234 A | 4/2015 |
| WO | WO-2009031771 A2 * | 3/2009 ............. A61B 1/045 |

OTHER PUBLICATIONS

Japanese Office Action dated Nov. 5, 2019 in Japanese Patent Application No. 2017-563410.

* cited by examiner

|  |  | PREVIOUS INSTRUCTION INFORMATION (FIRST) | |
|---|---|---|---|
|  |  | STOPPING | IMAGING |
| CURRENT INSTRUCTION INFORMATION (FRIST/SECOND) | STOPPING/ STOPPING | STOPPING | STOPPING |
|  | STOPPING/ IMAGING | STOPPING | STOPPING |
|  | IMAGING/ STOPPING | IMAGING | STOPPING |
|  | IMAGING/ IMAGING | IMAGING | IMAGING |

|  |  | PREVIOUS INSTRUCTION INFORMATION (THIRD) | |
|---|---|---|---|
|  |  | STOPPING | IMAGING |
| CURRENT INSTRUCTION INFORMATION (FIRST/SECOND) | STOPPING/STOPPING | STOPPING | STOPPING |
|  | STOPPING/IMAGING | STOPPING | STOPPING |
|  | IMAGING/STOPPING | IMAGING | STOPPING |
|  | IMAGING/IMAGING | IMAGING | IMAGING |

FIG. 7

|  |  | PREVIOUS INSTRUCTION INFORMATION (FIRST/SECOND) | | | |
|---|---|---|---|---|---|
|  |  | STOPPING/STOPPING | STOPPING/IMAGING | IMAGING/STOPPING | IMAGING/IMAGING |
| CURRENT INSTRUCTION INFORMATION (FIRST/SECOND) | STOPPING/STOPPING | STOPPING | STOPPING | STOPPING | STOPPING |
|  | STOPPING/IMAGING | STOPPING | STOPPING | STOPPING | IMAGING |
|  | IMAGING/STOPPING | IMAGING | IMAGING | STOPPING | STOPPING |
|  | IMAGING/IMAGING | IMAGING | IMAGING | IMAGING | IMAGING |
|  |  | C11 | C12 | C13 | C14 |

FIG. 8

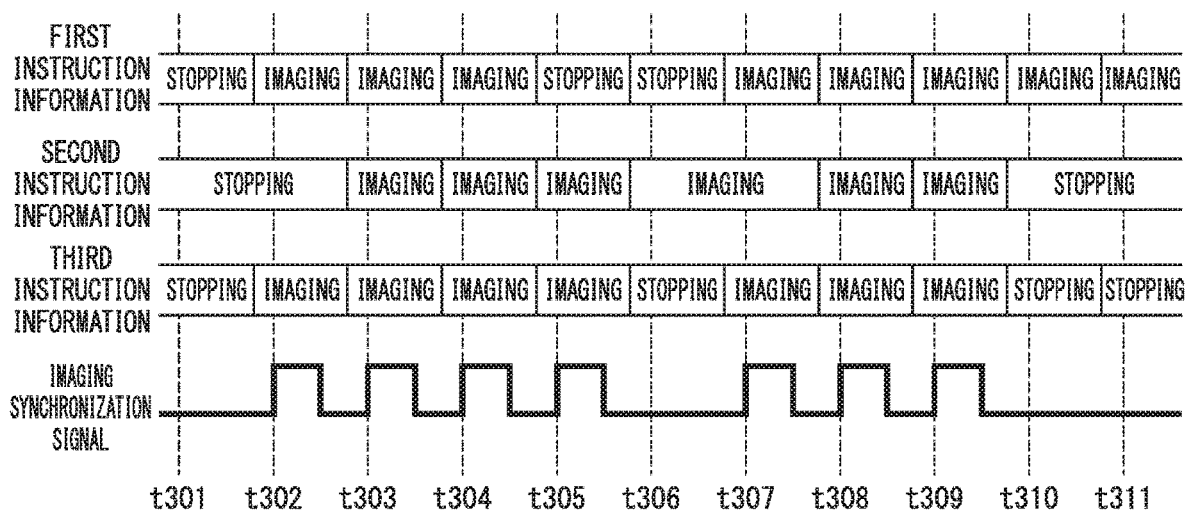

FIG. 9

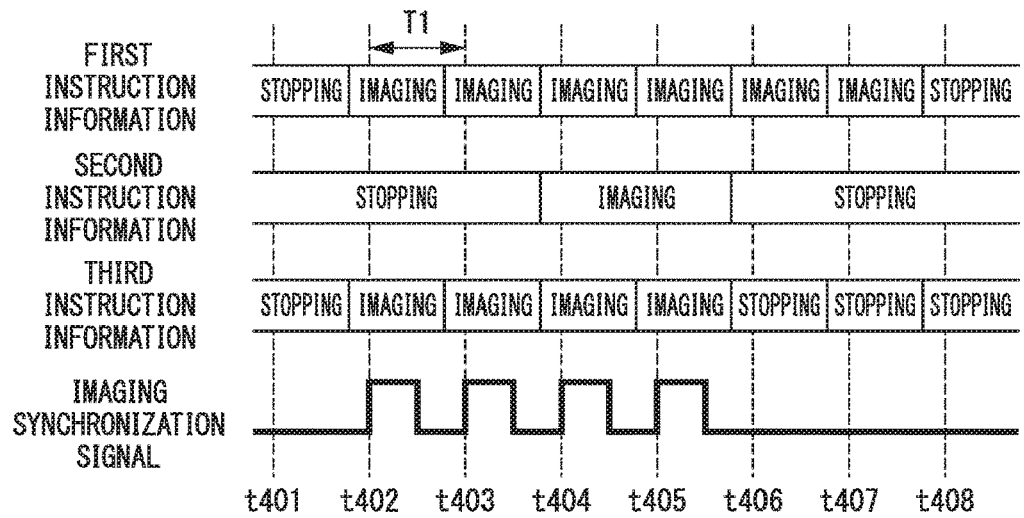

FIG. 10

|  |  | PREVIOUS INSTRUCTION INFORMATION (FIRST/SECOND) | | | |
|  |  | STOPPING/ STOPPING | STOPPING/ IMAGING | IMAGING/ STOPPING | IMAGING/ IMAGING |
| CURRENT INSTRUCTION INFORMATION (FIRST/SECOND) | STOPPING/ STOPPING | STOPPING | STOPPING | STOPPING | STOPPING |
|  | STOPPING/ IMAGING | IMAGING | IMAGING | IMAGING | IMAGING |
|  | IMAGING/ STOPPING | IMAGING | IMAGING | IMAGING | STOPPING |
|  | IMAGING/ IMAGING | IMAGING | IMAGING | IMAGING | IMAGING |
|  |  | C21 | C22 | C23 | C24 |

FIG. 11

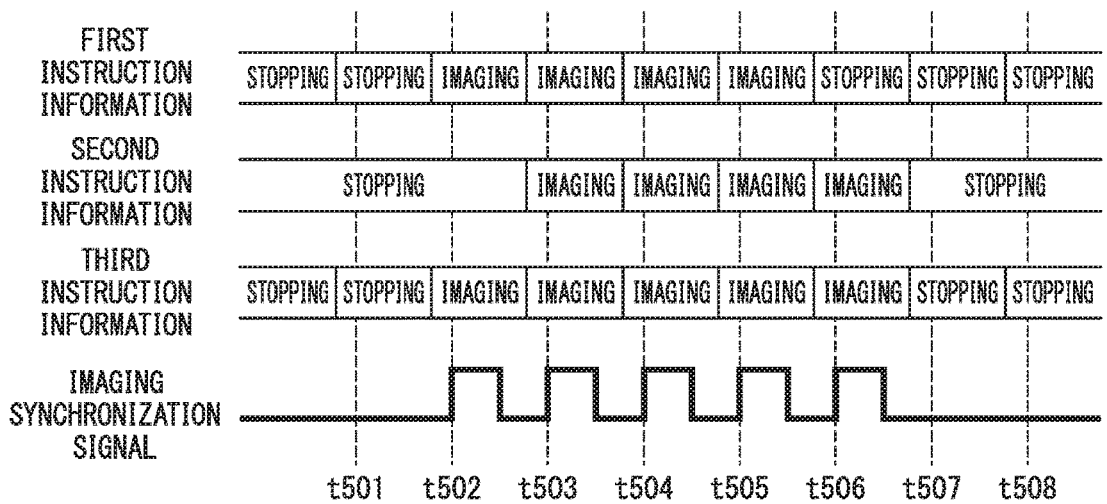

FIG. 13

|  |  | PREVIOUS INSTRUCTION INFORMATION (FIRST/SECOND) | | | | | |
|---|---|---|---|---|---|---|---|
|  |  | L/M | L/H | M/M | M/H | H/M | H/H |
| CURRENT INSTRUCTION INFORMATION (FIRST/SECOND) | L/M | L | L | L | L | L | L |
|  | L/H | L | L | L | L | L | L |
|  | M/M | M | M | M | M | M | M |
|  | M/H | M | M | M | M | M | M |
|  | H/M | H | H | H | H | RETENTION | M |
|  | H/H | H | H | H | H | H | H |

CAPSULE ENDOSCOPE HAVING IMAGING SYNCHRONIZATION BASED ON DATA FROM AN IMAGE SENSOR AND ANOTHER SENSOR

This application is a continuation application based on International Patent Application No. PCT/JP2016/051966, filed on Jan. 25, 2016, the content of which is incorporated herein by reference.

BACKGROUND OF THE INVENTION

Field of the Invention

The present invention relates to a capsule endoscope.

Description of Related Art

When a capsule endoscope passes through an organ of an examinee, the capsule endoscope moves relative to a human body. In a case in which a moving velocity thereof is fast, an imaging frame rate of the capsule endoscope is preferably raised to reduce failure of imaging the test subject. In addition, when the capsule endoscope is stopped relative to the human body, the imaging frame rate of the capsule endoscope is preferably lowered to reduce power consumption.

In a system disclosed in U.S. Pat. No. 6,709,387, the imaging frame rate is determined on the basis of an output of a sensor that detects movement of a capsule. The system can also determine the imaging frame rate on the basis of a comparison result of two images output from the capsule. A device external to the capsule determines the frame rate, and the capsule is instructed of the frame rate that is determined.

A system disclosed in Japanese Unexamined Patent Application, First Publication No. 2009-195271 includes two acceleration sensors. An acceleration sensor provided in the capsule endoscope detects an acceleration of the capsule endoscope. An acceleration sensor provided in a reception device detects an acceleration of a human body into which the capsule endoscope is inserted. The system disclosed in Japanese Unexamined Patent Application, First Publication No. 2009-195271 detects relative movement of the capsule endoscope with respect to the human body on the basis of outputs of the two acceleration sensors. In the system disclosed in Japanese Unexamined Patent Application, First Publication No. 2009-195271, at least one of the capsule endoscope and the reception device includes a determination unit that determines the imaging frame rate on the basis of the movement that is detected.

SUMMARY OF THE INVENTION

According to a first aspect of the present invention, a capsule endoscope is provided, including a first sensor, a second sensor, an information generator, a signal generator, and an imager. The first sensor generates first data. The second sensor generates second data different from the first data. The information generator generates third instruction information on the basis of at least one of first instruction information and second instruction information. The first instruction information is an analysis result of the first data. The second instruction information is an analysis result of the second data. The signal generator generates an imaging synchronization signal on the basis of the third instruction information. The imager performs imaging on the basis of the imaging synchronization signal and acquires an image.

An update interval of the first instruction information is equal to or shorter than an update interval of the second instruction information. The information generator generates the third instruction information on the basis of a combination of at least three pieces of instruction information. The at least three pieces of instruction information include at least one of the first instruction information at a first time point and the second instruction information at the first time point. The at least three pieces of instruction information include at least one of the first instruction information at a second time point, the second instruction information at the second time point, and the third instruction information at the second time point. The second time point is a time point before the first time point.

According to a second aspect of the present invention, in the first aspect, the second sensor may be the imager, and the second data may be the image.

According to a third aspect of the present invention, in the first or second aspect, the information generator may retain the generated third instruction information regardless of contents of the first instruction information until the second instruction information is generated.

According to a fourth aspect of the present invention, in any one of the first to third aspects, the information generator may generate the third instruction information on the basis of state information. In the state information, the first instruction information at the first time point and the second instruction information at the first time point, the first instruction information at the second time point and the second instruction information at the second time point, and the third instruction information to be generated may be correlated with each other. In the state information, the number of pieces of the third instruction information that causes an imaging frequency to become relatively low may be greater than the number of pieces of the third instruction information that causes the imaging frequency to become relatively high.

According to a fifth aspect of the present invention, in any one of the first to third aspects, the information generator may generate the third instruction information on the basis of state information. In the state information, the first instruction information at the first time point and the second instruction information at the first time point, the first instruction information at the second time point and the second instruction information at the second time point, and the third instruction information to be generated may be correlated with each other. In the state information, the number of pieces of the third instruction information that causes an imaging frequency to become relatively high may be greater than the number of pieces of the third instruction information that causes the imaging frequency to become relatively low.

According to a sixth aspect of the present invention, in any one of the first to fifth aspects, at least one of the first instruction information and the second instruction information may represent any one of three or more values, and the third instruction information may represent any one of the three or more values.

According to a seventh aspect of the present invention in any one of the first to sixth aspects, the capsule endoscope may further include a counter of which a count value increases or decreases from a reference value. The count value may be calculated on the basis of the third instruction information each time the first instruction information is updated. When the imaging synchronization signal is generated, the count value may become the reference value. When the count value increases from the reference value and the count value becomes equal to or greater than a predetermined value, or when the count value decreases from the reference value and the count value becomes equal to or less than the predetermined value, the signal generator may generate the imaging synchronization signal.

According to an eighth aspect of the present invention in any one of the first to seventh aspects, the capsule endoscope may further include a communicator that performs radio communication with a radio communication device. The communicator may transmit at least one of the first data and the second data to the radio communication device. When the communicator transmits the first data to the radio communication device, the communicator receives the first instruction information from the radio communication device. When the communicator transmits the second data to the radio communication device, the communicator receives the second instruction information from the radio communication device.

BRIEF DESCRIPTION OF THE DRAWINGS

FIG. 6 is a table showing state information in a third operation of the capsule endoscope according to the first embodiment of the present invention.

FIG. 7 is a table showing state information in a fourth operation of the capsule endoscope according to the first embodiment of the present invention.

FIG. 8 is a timing chart showing the fourth operation of the capsule endoscope according to the first embodiment of the present invention.

FIG. 9 is a timing chart showing a fifth operation of the capsule endoscope according to the first embodiment of the present invention.

FIG. 10 is a table showing state information in a sixth operation of the capsule endoscope according to the first embodiment of the present invention.

FIG. 11 is a timing chart showing the sixth operation of the capsule endoscope according to the first embodiment of the present invention.

FIG. 13 is a table showing state information in the capsule endoscope according to the modification example of the first embodiment of the present invention.

DETAILED DESCRIPTION OF THE INVENTION

Embodiments of the present invention will be described with reference to the drawings.

First Embodiment

Figure 1:
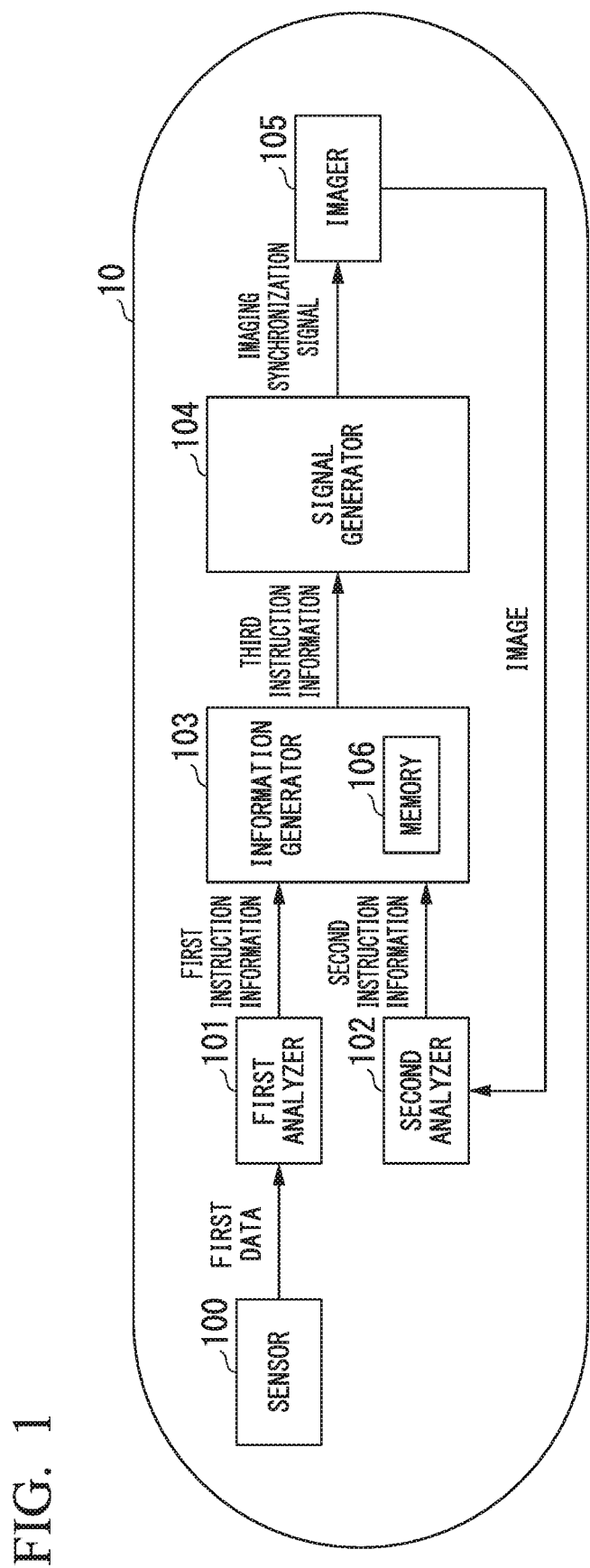
FIG. 1 is a block diagram showing a configuration of a capsule endoscope according to a first embodiment of the present invention.

FIG. 1 shows a configuration of a capsule endoscope 10 according to a first embodiment of the present invention. As shown in FIG. 1, the capsule endoscope 10 includes a sensor 100, a first analyzer 101, a second analyzer 102, an information generator 103, a signal generator 104, and an imager 105. Each of the configurations shown in FIG. 1 is constituted by hardware.

The sensor 100 (first sensor) generates first data. The imager 105 (second sensor) generates second data different from the first data. The information generator 103 generates third instruction information on the basis of at least one of first instruction information and second instruction information. The first instruction information is an analysis result of the first data. The second instruction information is an analysis result of the second data. The signal generator 104 generates an imaging synchronization signal on the basis of the third instruction information. The imager 105 performs imaging on the basis of the imaging synchronization signal and acquires an image. An update interval of the first instruction information is equal to or shorter than an update interval of the second instruction information. The information generator 103 generates the third instruction information on the basis of a combination of at least three pieces of instruction information. The at least three pieces of instruction information include at least one of the first instruction information and the second instruction information at a first time point, and at least one of the first instruction information, the second instruction information, and the third instruction information at a second time point. The second time point is a time point before the first time point.

Details of the respective configurations shown in FIG. 1 will be described. The sensor 100 periodically detects a physical amount at an interval of a first time, and generates first data representing the physical amount that is detected. A period of generating the first data by the sensor 100 is the same as the first time. For example, the sensor 100 is a movement sensor. The sensor 100 periodically detects movement of the capsule endoscope 10 at the interval of the first time, and generates first data representing the detected movement of the capsule endoscope 10. For example, the sensor 100 is at least one of an acceleration sensor, a velocity sensor, a magnetic sensor, and an angular velocity sensor. Accordingly, the sensor 100 can acquire data on at least one of acceleration, velocity, angular velocity, and magnetism. The sensor 100 outputs the first data to the first analyzer 101.

In a case in which the sensor 100 is the acceleration sensor, the first data is acceleration data. The acceleration data is a result obtained by measuring acceleration of the capsule endoscope 10.

In a case in which the sensor 100 is the velocity sensor, the first data is velocity data. The velocity data is a result obtained by measuring the velocity of the capsule endoscope 10.

Position data may be obtained by integrating the velocity represented by the velocity data. It is possible to detect movement of the capsule endoscope 10 from a variation amount of the position data at a plurality of times.

In a case in which the sensor 100 is the magnetic sensor, the first data is magnetic data. The magnetic data is a result obtained by measuring the Earth's magnetism. When using a magnetic sensor that can perform measurement in a three-dimensional direction, it is also possible to detect a posture of the capsule endoscope 10. Accordingly, it is also possible to detect movement of the capsule endoscope 10 from a variation amount of the magnetic data at a plurality of times.

In a case in which the sensor 100 is the angular velocity sensor, the first data is angular velocity data. The angular velocity data is a result obtained by measuring the angular velocity of the capsule endoscope 10.

The first analyzer 101 is constituted by one or a plurality of processors. The processors include a central processing unit (CPU), a digital signal processor (DSP), an application specific integrated circuit (ASIC), a field-programmable gate array (FPGA), and the like. The first analyzer 101 analyzes the first data and generates the first instruction information representing an analysis result. The first analyzer 101 outputs the first instruction information to the information generator 103.

For example, the first analyzer 101 compares the first data and a predetermined threshold value with each other, or compares a variation amount of the first data at a plurality of times and a predetermined threshold value. In a case in which the first data is the acceleration data, the first analyzer 101 may calculate velocity data or position data on the basis of the acceleration data. The first instruction information is a result of the above-described comparison.

The sensor 100 may periodically detect movement of the capsule endoscope 10 at an interval of a second time. The second time is equal to or shorter than the first time. The first analyzer 101 may analyze the movement detected by the sensor 100, and periodically generate the first data based on the movement at the first time interval.

The second analyzer 102 is constituted by one or a plurality of processors. The second analyzer 102 analyzes the second data and generates the second instruction information that represents an analysis result. The second analyzer 102 outputs the second instruction information to the information generator 103. The capsule endoscope 10 includes two sensors. A first sensor is the sensor 100, and a second sensor is the imager 105. The second data is an image that is acquired by the imager 105.

The information generator 103 (information generation circuit) is constituted by one or a plurality of processors. The information generator 103 generates the third instruction information on the basis of a combination of instruction information at two different points of time. For example, the information generator 103 periodically generates the third instruction information at an interval of the first time. That is, the information generator 103 generates the third instruction information at a period in which the first instruction information is updated. Hereinafter, the first time point is a current time point. Specifically, the current time point is a time point before the first time has elapsed from a time point immediately after the third instruction information is generated. Hereinafter, the second time point is a previous time point. Specifically, the previous time point is a time point at which the third instruction information is immediately previously generated. That is, the previous time point is a time point before a time point, at which the third instruction information is to be generated, by the first time.

The information generator 103 includes a memory 106. The memory 106 is a nonvolatile recording medium. The memory 106 stores state information in which a combination of a plurality of pieces of instruction information at two different points of time and the third instruction information to be generated are correlated with each other. In addition, the memory 106 stores previous instruction information. The memory 106 is provided in the information generator 103. The memory 106 may be independent from the information generator 103.

The signal generator 104 (signal generation circuit) is a digital signal processing circuit. The signal generator 104 may be constituted by one or a plurality of processors. For example, the signal generator 104 periodically refers to the third instruction information at the interval of the first time, and generates the imaging synchronization signal on the basis of the third instruction information. At least two of the first analyzer 101, the second analyzer 102, the information generator 103, and the signal generator 104 may be constituted by one piece of hardware.

The imager 105 is an imaging element (image sensor). The imager 105 performs imaging at an imaging timing based on the imaging synchronization signal, and acquires an image (image data). A test subject that is imaged by the imager 105 is an organ in the human body. The image acquired by the imager 105 may be wirelessly transmitted to a reception device at the outside of the body.

For example, the functions of the first analyzer 101, the second analyzer 102, the information generator 103, and the signal generator 104 can be realized as a software function when a computer of the capsule endoscope 10 reads out and executes a program including commands which define operations of the units. For example, the program may be provided by a "computer-readable recording medium" such as a flash memory. In addition, the above-described program may be transmitted to the capsule endoscope 10 through a transmission medium or by transmission waves in the transmission medium from a computer including a storage device in which the program is stored, and the like. The "transmission medium" through which the program is transmitted is a medium that has an information transmission function such as a network (communication network) such as the Internet, and a communication channel (communication line) such as telephone line. In addition, the above-described program may realize some of the above-described functions. In addition, the above-described program may be a differential file (differential program) that can realize the above-described functions in a combination with a program that is recorded in the computer in advance.

First Operation

Figures 2, 3:
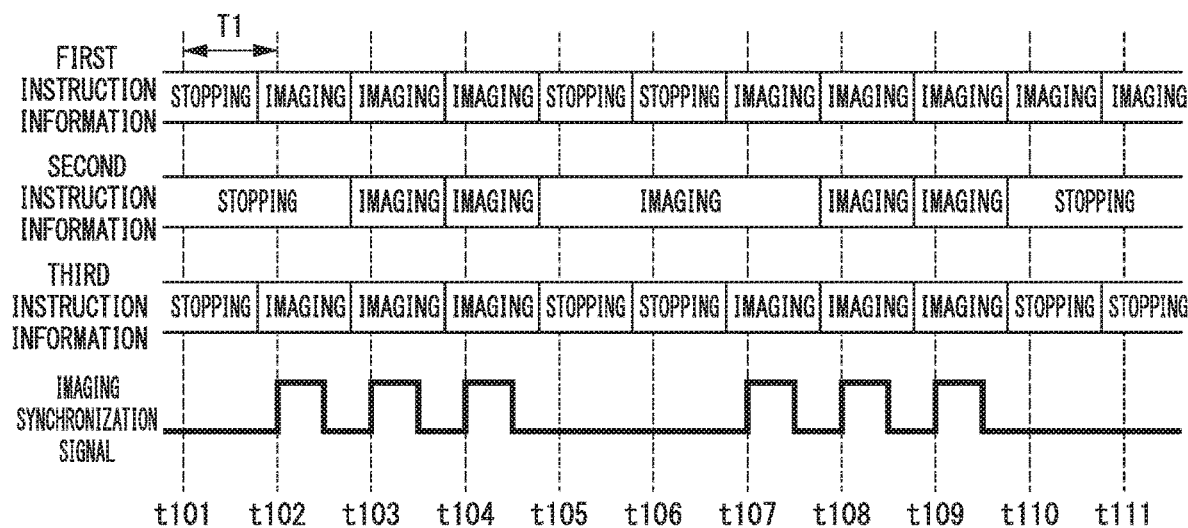
FIG. 2 is a table showing state information in a first operation of the capsule endoscope according to the first embodiment of the present invention.
FIG. 3 is a timing chart showing the first operation of the capsule endoscope according to the first embodiment of the present invention.

In a first operation, the information generator 103 generates the third instruction information on the basis of current first instruction information, current second instruction information, and previous first instruction information. FIG. 2 shows state information in the first operation. In FIG. 2, the state information is shown as a table. A current first instruction information state, a current second instruction information state, a previous first instruction information state, and a third instruction information state are correlated with each other. Respective pieces of instruction information represent any one value between two values. The two values include "imaging" and "stopping". "Imaging" represents an imaging instruction to the imager 105. That is, "imaging" represents a state in which an imaging frequency is relatively high. "Stopping" represents an imaging stopping instruction to the imager 105. That is, "stopping" represents a state in which an imaging frequency is relatively low.

In a case in which movement of the capsule endoscope 10 which is detected from the first data is relatively large, the first instruction information is "imaging". In a case in which movement of the capsule endoscope 10 which is detected from the first data is relatively small, the first instruction information is "stopping". In a case in which movement of the capsule endoscope 10 which is detected from the second data, that is, an image is relatively large, the second instruction information is "imaging". In a case in which movement of the capsule endoscope 10 which is detected from the second data, that is, an image is relatively small, the second instruction information is "stopping".

A current first instruction information state and a current second instruction information state are marked by "/". A left side of "/" is the first instruction information state, and a right side of "/" is the second instruction information state. For example, "stopping/imaging" represents that the first instruction information is "stopping" and the second instruction information is "imaging". The current first instruction information state and the current second instruction information state, and the third instruction information corresponding thereto are described in the same row. A previous first instruction information state and the third instruction information corresponding thereto are described in the same column. For example, in a case in which the current first instruction information and the current second instruction information are "stopping/imaging" and the previous first instruction information is "stopping", the third instruction information that is generated by the information generator 103 is "stopping".

In a case in which the current first instruction information is "stopping", movement detected by the sensor 100 is small. That is, there is a high possibility that the capsule endoscope 10 is stopped. In this case, the third instruction information is set to "stopping". In a case in which the current first instruction information is "stopping" and the current second instruction information is "imaging", there is a possibility that large movement is detected from an image before stoppage of the capsule endoscope 10.

In a case in which the current first instruction information is "imaging", the current second instruction information is "stopping", and the previous first instruction information is "stopping", movement detected by the sensor 100 greatly increases. In this case, there is a possibility that the capsule endoscope 10 that is stopped may initiate movement. Accordingly, the third instruction information is set to "imaging" to reduce failure of imaging the test subject.

In a case in which the current first instruction information is "imaging", the current second instruction information is "stopping", and the previous first instruction information is "imaging", movement detected by the sensor 100 is large, and movement detected from an image is small. In this case, there is a possibility that the capsule endoscope 10 is stopped with respect to a human body, and the human body is moving. Accordingly, the third instruction information is set to "stopping" to suppress unnecessary imaging.

In a case in which the current first instruction information and the current second instruction information are "imaging", both the movement detected by the sensor 100 and the movement detected from an image are large. That is, there is a high possibility that the capsule endoscope 10 is moving. In this case, the third instruction information is set to "imaging".

In the first operation, in a case in which the current first instruction information and the current second instruction information represent a relatively low imaging frequency ("stopping"), the third instruction information represents a relatively low imaging frequency ("stopping"). In a case in which the current first instruction information represents a relatively low imaging frequency ("stopping"), and the current second instruction information represents a relatively high imaging frequency ("imaging"), the third instruction information represents a relatively low imaging frequency ("stopping"). In a case in which the current first instruction information represents a relatively high imaging frequency ("imaging"), and the current second instruction information represents a relatively low imaging frequency ("stopping"), the third instruction information is based on the previous first instruction information. In a case in which the current first instruction information represents a relatively high imaging frequency ("imaging"), the current second instruction information represents a relatively low imaging frequency ("stopping"), and the previous first instruction information represents a relatively low imaging frequency ("stopping"), the third instruction information represents a relatively high imaging frequency ("imaging"). In a case in which the current first instruction information represents a relatively high imaging frequency ("imaging"), the current second instruction information represents a relatively low imaging frequency ("stopping"), and the previous first instruction information represents a relatively high imaging frequency ("imaging"), the third instruction information represents a relatively low imaging frequency ("stopping"). In a case in which the current first instruction information and the current second instruction information represent a relatively high imaging frequency ("imaging"), the third instruction information represents a relatively high imaging frequency ("imaging").

FIG. 3 shows the first operation of the capsule endoscope 10. In FIG. 3, a first instruction information state, a second instruction information state, a third instruction information state, and a waveform of the imaging synchronization signal are shown. With regard to the imaging synchronization signal, a vertical direction in FIG. 3 represents a voltage. Time proceeds to the right in FIG. 3.

The first instruction information is updated at an interval of a first time T1. The updated first instruction information may become the same as the first instruction information before updating. A position at which the first instruction information shown in FIG. 3 is marked represents a time point at which the first instruction information is newly generated and thus the first instruction information is updated.

The imaging synchronization signal has a high level and a low level. When the imaging synchronization signal is at the high level, the imaging synchronization signal is valid. When the imaging synchronization signal is at the low level, the imaging synchronization signal is invalid. When the imaging synchronization signal is valid, the imager 105 performs imaging. The imaging synchronization signal may be valid when the imaging synchronization signal is at the low level, and the imaging synchronization signal may be invalid when the imaging synchronization signal is at the high level.

The second instruction information is updated after the imaging is performed by the imager 105. That is, the second instruction information is updated after the imaging synchronization signal at the high level is generated. The updated second instruction information may become the same as the second instruction information before updating. A position at which the second instruction information shown in FIG. 3 is marked represents a time point at which the second instruction information is newly generated and thus the second instruction information is updated. The second instruction information is updated at an interval that is equal to or longer than the first time T1. That is, an updating frequency of the second instruction information is equal to or less than an updating frequency of the first instruction information.

The third instruction information is updated at an interval of the first time T1. The updated third instruction information may become the same as the third instruction information before updating. A position at which the third instruction information shown in FIG. 3 is marked represents a time point at which the third instruction information is newly generated and thus the third instruction information is updated.

At a timing t101, the first instruction information, the second instruction information, and the third instruction information are "stopping", and the imaging synchronization signal is invalid.

After the timing t101, the first instruction information is changed to "imaging". At this time, the current first instruction information and the current second instruction information are "imaging/stopping", and the previous first instruction information is "stopping". In this case, there is a possibility that the capsule endoscope 10 that is stopped may initiate movement. According to this, the information generator 103 sets the third instruction information to "imaging". At a timing t102, the signal generator 104 generates a valid imaging synchronization signal. Accordingly, failure of imaging the test subject is suppressed.

After the timing t102, the second instruction information is changed to "imaging". At this time, the current first instruction information and the current second instruction information are "imaging/imaging", and the previous first instruction information is "imaging". According to this, the information generator 103 sets the third instruction information to "imaging". At a timing t103, the signal generator 104 generates a valid imaging synchronization signal.

At a timing t104, respective pieces of instruction information are the same as respective pieces of instruction information at the timing at t103. At the timing t104, the signal generator 104 generates a valid imaging synchronization signal.

After the timing t104, the first instruction information is changed to "stopping". At this time, the current first instruction information and the current second instruction information are "stopping/imaging", and the previous first instruction information is "imaging". In this case, there is a possibility that the capsule endoscope 10 that is moving may terminate movement. According to this, the information generator 103 sets the third instruction information to "stopping". At a timing t105, the imaging synchronization signal is invalid. According to this, unnecessary imaging is suppressed.

At a timing t106, respective pieces of instruction information are the same as respective pieces of instruction information at the timing t105. At the timing t106, the imaging synchronization signal is invalid.

At a timing t107, a timing t108, and a timing t109, the current first instruction information and the current second instruction information are "imaging/imaging". At the timings, the third instruction information is "imaging". At the timings, the signal generator 104 generates a valid imaging synchronization signal.

After the timing t109, the second instruction information is changed to "stopping". At this time, the current first instruction information and the current second instruction information are "imaging/stopping", and the previous first instruction information is "imaging". In this case, there is a possibility that the capsule endoscope 10 is stopped with respect to the human body, and the human body is moving. According to this, the information generator 103 sets the third instruction information to "stopping". At a timing t110, the imaging synchronization signal is invalid. According to this, unnecessary imaging is suppressed.

At a timing t111, respective pieces of instruction information are the same as respective pieces of instruction information at the timing t110. At the timing t111, the imaging synchronization signal is invalid.

In the first operation, when the first instruction information is changed from "stopping" to "imaging", the third instruction information is set to "imaging", and thus failure of imaging the test subject is suppressed. When the first instruction information is continuously "imaging" and the second instruction information is "stopping", the third instruction information is set to "stopping", and thus unnecessary imaging is suppressed. As a result, power consumption of the capsule endoscope 10 is reduced.

Second Operation

Figures 4, 5:
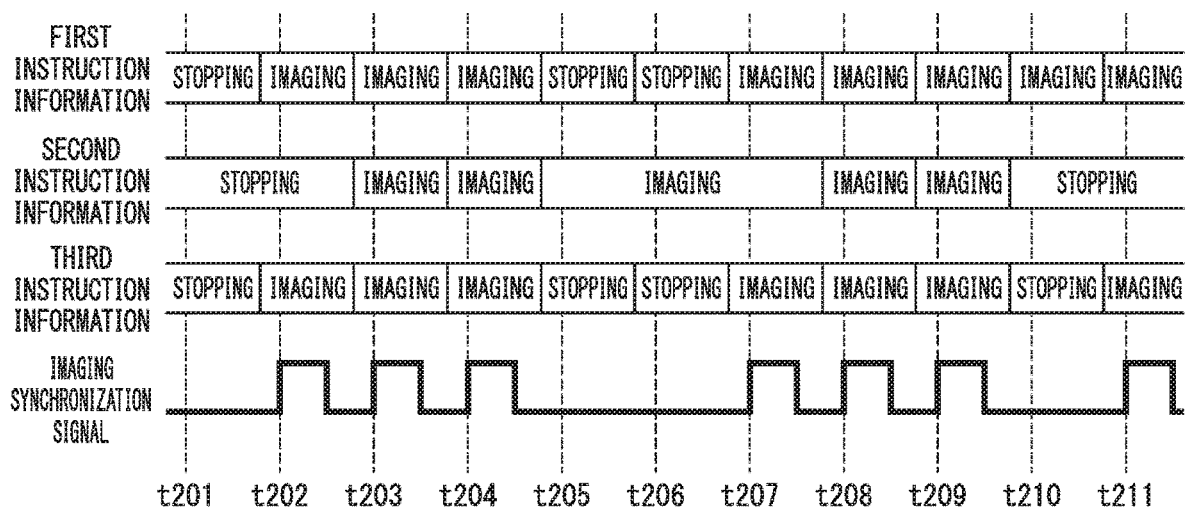
FIG. 4 is a table showing state information in a second operation of the capsule endoscope according to the first embodiment of the present invention.
FIG. 5 is a timing chart showing the second operation of the capsule endoscope according to the first embodiment of the present invention.

In a second operation, the information generator 103 generates the third instruction information on the basis of current first instruction information, current second instruction information, and previous second instruction information. FIG. 4 shows state information in the second operation. In FIG. 4, the state information is shown as a table. A current first instruction information state, a current second instruction information state, a previous second instruction information state, and a third instruction information state are correlated with each other. Respective pieces of instruction information represent any one value between two values. The two values include "imaging" and "stopping".

A current first instruction information state and a current second instruction information state, and the third instruction information corresponding thereto are described in the same row. A previous second instruction information state and the third instruction information corresponding thereto are described in the same column. For example, in a case in which the current first instruction information and the current second instruction information are "stopping/imaging" and the previous second instruction information is "stopping", the third instruction information that is generated by the information generator 103 is "stopping".

In a case in which the current first instruction information is "stopping", movement detected by the sensor 100 is small. That is, there is a high possibility that the capsule endoscope 10 is stopped. In this case, the third instruction information is set to "stopping". In a case in which the current first instruction information is "stopping" and the current second instruction information is "imaging", there is a possibility that large movement is detected from an image before stoppage of the capsule endoscope 10.

In a case in which the current first instruction information is "imaging", the current second instruction information is "stopping", and the previous second instruction information is "stopping", movement detected from an image is small, and movement detected by the sensor 100 is large. In this case, there is a possibility that the capsule endoscope 10 is stopped with respect to the human body, and the human body is moving. However, the third instruction information is set to "imaging" to confirm whether or not the capsule endoscope 10 is moving by an image.

In a case in which the current first instruction information is "imaging", the current second instruction information is "stopping", and the previous second instruction information is "imaging", movement detected from an image is greatly reduced. In this case, there is a possibility that the moving capsule endoscope 10 may terminate movement. In addition, since the current first instruction information is "imaging", movement detected by the sensor 100 is large. In this case, there is a possibility that the capsule endoscope 10 is stopped with respect to the human body, and the human body is moving. Accordingly, the third instruction information is set to "stopping" to suppress unnecessary imaging.

In a case in which the current first instruction information and the current second instruction information are "imaging", both the movement detected by the sensor 100 and the movement detected from an image are large. That is, there is a high possibility that the capsule endoscope 10 is moving. In this case, the third instruction information is set to "imaging".

In the second operation, in a case in which the current first instruction information and the current second instruction information represent a relatively low imaging frequency ("stopping"), the third instruction information represents a relatively low imaging frequency ("stopping"). In a case in which the current first instruction information represents a relatively low imaging frequency ("stopping"), and the current second instruction information represents a relatively high imaging frequency ("imaging"), the third instruction information represents a relatively low imaging frequency ("stopping"). In a case in which the current first instruction information represents a relatively high imaging frequency ("imaging"), and the current second instruction information represents a relatively low imaging frequency ("stopping"), the third instruction information is based on the previous second instruction information. In a case in which the current first instruction information represents a relatively high imaging frequency ("imaging"), the current second instruction information represents a relatively low imaging frequency ("stopping"), and the previous second instruction information represents a relatively low imaging frequency ("stopping"), the third instruction information represents a relatively high imaging frequency ("imaging"). In a case in which the current first instruction information represents a relatively high imaging frequency ("imaging"), the current second instruction information represents a relatively low imaging frequency ("stopping"), and the previous second instruction information represents a relatively high imaging frequency ("imaging"), the third instruction information represents a relatively low imaging frequency ("stopping"). In a case in which the current first instruction information and the current second instruction information represent a relatively high imaging frequency ("imaging"), the third instruction information represents a relatively high imaging frequency ("imaging").

FIG. 5 shows the second operation of the capsule endoscope 10. In FIG. 5, the first instruction information state, the second instruction information state, the third instruction information state, and a waveform of the imaging synchronization signal are shown. With regard to the imaging synchronization signal, a vertical direction in FIG. 5 represents a voltage. Time proceeds to the right in FIG. 5.

At a timing t201, the first instruction information, the second instruction information, and the third instruction information are "stopping", and the imaging synchronization signal is invalid.

After the timing t201, the first instruction information is changed to "imaging". At this time, the current first instruction information and the current second instruction information are "imaging/stopping", and the previous second instruction information is "stopping". In this case, there is a possibility that the capsule endoscope 10 that is stopped may initiate movement. According to this, the information generator 103 sets the third instruction information to "imaging". At a timing t202, the signal generator 104 generates a valid imaging synchronization signal. Accordingly, failure of imaging the test subject is suppressed.

After the timing t202, the second instruction information is changed to "imaging". At this time, the current first instruction information and the current second instruction information are "imaging/imaging", and the previous second instruction information is "stopping". According to this, the information generator 103 sets the third instruction information to "imaging". At a timing t203, the signal generator 104 generates a valid imaging synchronization signal.

At a timing t204, respective pieces of instruction information are the same as respective pieces of instruction information at the timing at t203. At the timing t204, the signal generator 104 generates a valid imaging synchronization signal.

After the timing t204, the first instruction information is changed to "stopping". At this time, the current first instruction information and the current second instruction information are "stopping/imaging", and the previous second instruction information is "imaging". In this case, there is a possibility that the capsule endoscope 10 that is moving may terminate movement. According to this, the information generator 103 sets the third instruction information to "stopping". At a timing t205, the imaging synchronization signal is invalid. According to this, unnecessary imaging is suppressed.

At a timing t206, respective pieces of instruction information are the same as respective pieces of instruction information at the timing t205. At the timing t206, the imaging synchronization signal is invalid.

At a timing t207, a timing t208, and a timing t209, the current first instruction information and the current second instruction information are "imaging/imaging". At the timings, the third instruction information is "imaging". At the timings, the signal generator 104 generates a valid imaging synchronization signal.

After the timing t209, the second instruction information is changed to "stopping". At this time, the current first instruction information and the current second instruction information are "imaging/stopping", and the previous second instruction information is "imaging". In this case, there is a possibility that the capsule endoscope 10 is stopped with respect to the human body, and the human body is moving. According to this, the information generator 103 sets the third instruction information to "stopping". At a timing t210, the imaging synchronization signal is invalid. According to this, unnecessary imaging is suppressed.

After the timing t210, the current first instruction information and the current second instruction information are "imaging/stopping", and the previous second instruction information is "stopping". In this case, there is a possibility that the capsule endoscope 10 is stopped with respect to the human body, and the human body is moving. However, the information generator 103 sets the third instruction information to "imaging". At a timing t211, the signal generator 104 generates a valid imaging synchronization signal. According to this, imaging is performed by the imager 105, and an image is acquired. The second analyzer 102 can confirm whether or not the capsule endoscope 10 is moving with respect to the human body on the basis of the image.

In the second operation, when the second instruction information is changed from "imaging" to "stopping", the third instruction information is set to "stopping", and thus unnecessary imaging is suppressed. As a result, power consumption of the capsule endoscope 10 is reduced. When the second instruction information is continuously "stopping" and the first instruction information is "imaging", the third instruction information is set to "imaging". According to this, an image, which is used to confirm whether or not the capsule endoscope 10 is moving with respect to the human body is acquired.

In the first operation shown in FIG. 4 and the second operation shown in FIG. 5, the third instruction information at the timing t111 and the third instruction information at the timing t211 are different from each other. In the second operation, priority is given to suppression of failure of imaging the test subject rather than suppression of unnecessary imaging.

Third Operation

In a third operation, the information generator 103 generates the third instruction information on the basis of the current first instruction information, the current second instruction information, and the previous third instruction information. FIG. 6 shows state information in the third operation. In FIG. 6, state information is shown as a table. A current first instruction information state, a current second instruction information state, a previous third instruction information state, and a third instruction information state after updating are correlated with each other. Respective pieces of instruction information represent any one value between two values. The two values include "imaging" and "stopping".

The current first instruction information state and the current second instruction information state, and the third instruction information corresponding thereto are described in the same row. The previous third instruction information state and the third instruction information after updating which corresponds thereto are described in the same column. For example, in a case in which the current first instruction information and the current second instruction information are "stopping/imaging", and the previous third instruction information is "stopping", the third instruction information generated by the information generator 103 is "stopping".

In a case in which the current first instruction information is "stopping", movement detected by the sensor 100 is small. That is, there is a high possibility that the capsule endoscope 10 is stopped. In this case, the third instruction information is set to "stopping". In a case in which the current first instruction information is "stopping" and the current second instruction information is "imaging", there is a possibility that large movement is detected from an image before stoppage of the capsule endoscope 10.

In a case in which the current first instruction information is "imaging" and the current second instruction information is "stopping", movement detected by the sensor 100 is large, and movement detected from an image is small. In this case, the third instruction information after updating is different depending on the previous third instruction information. In a case in which the previous third instruction information is "stopping", there is a possibility that the capsule endoscope 10 is stopped with respect to the human body, and the human body is moving. However, the third instruction information is set to "imaging" to confirm whether or not the capsule endoscope 10 is moving by the image. In a case in which the previous third instruction information is "imaging", there is a possibility that the capsule endoscope 10 is stopped with respect to the human body, and the human body is moving. Accordingly, the third instruction information is set to "stopping" to suppress unnecessary imaging.

In a case in which the current first instruction information and the current second instruction information are "imaging", both the movement detected by the sensor 100 and the movement detected by the image are large. That is, there is a high possibility that the capsule endoscope 10 is moving. In this case, the third instruction information is set to "imaging".

In the third operation, in a case in which the current first instruction information and the current second instruction information represent a relatively low imaging frequency ("stopping"), the third instruction information represents a relatively low imaging frequency ("stopping"). In a case in which the current first instruction information represents a relatively low imaging frequency ("stopping"), and the current second instruction information represents a relatively high imaging frequency ("imaging"), the third instruction information represents a relatively low imaging frequency ("stopping"). In a case in which the current first instruction information represents a relatively high imaging frequency ("imaging"), and the current second instruction information represents a relatively low imaging frequency ("stopping"), the third instruction information is based on the previous third instruction information. In a case in which the current first instruction information represents a relatively high imaging frequency ("imaging"), the current second instruction information represents a relatively low imaging frequency ("stopping"), and the previous third instruction information represents a relatively low imaging frequency ("stopping"), the third instruction information after updating represents a relatively high imaging frequency ("imaging"). In a case in which the current first instruction information represents a relatively high imaging frequency ("imaging"), the current second instruction information represents a relatively low imaging frequency ("stopping"), and the previous third instruction information represents a relatively high imaging frequency ("imaging"), the third instruction information after updating represents a relatively low imaging frequency ("stopping"). In a case in which the current first instruction information and the current second instruction information represent a relatively high imaging frequency ("imaging"), the third instruction information represents a relatively high imaging frequency ("imaging").

The third operation will be described with reference to FIG. 5. At the timing t201, the first instruction information, the second instruction information, and the third instruction information are "stopping", and the imaging synchronization signal is invalid.

After the timing t201, the first instruction information is changed to "imaging". At this time, the current first instruction information and the current second instruction information are "imaging/stopping", and the previous third instruction information is "stopping". In this case, there is a possibility that the capsule endoscope 10 that is stopped may initiate movement. According to this, the information generator 103 sets the third instruction information to "imaging". At a timing t202, the signal generator 104 generates a valid imaging synchronization signal. Accordingly, failure of imaging the test subject is suppressed.

After the timing t202, the second instruction information is changed to "imaging". At this time, the current first instruction information and the current second instruction information are "imaging/imaging", and the previous third instruction information is "imaging". According to this, the information generator 103 sets the third instruction information to "imaging". At a timing t203, the signal generator 104 generates a valid imaging synchronization signal.

At a timing t204, respective pieces of instruction information are the same as respective pieces of instruction information at the timing at t203. At the timing t204, the signal generator 104 generates a valid imaging synchronization signal.

After the timing t204, the first instruction information is changed to "stopping". At this time, the current first instruction information and the current second instruction information are "stopping/imaging", and the previous third instruction information is "imaging". In this case, there is a possibility that the capsule endoscope 10 that is moving may terminate movement. According to this, the information generator 103 sets the third instruction information to "stopping". At a timing t205, the imaging synchronization signal is invalid. According to this, unnecessary imaging is suppressed.

After the timing t205, the current first instruction information and the current second instruction information are "stopping/imaging", and the previous third instruction information is "stopping". According to this, the information generator 103 sets the third instruction information to "stopping". At the timing t206, the imaging synchronization signal is invalid.

After the timing t206, the first instruction information is changed to "imaging". At this time, the current first instruction information and the current second instruction information are "imaging/imaging", and the previous third instruction information is "stopping". According to this, the information generator 103 sets the third instruction information to "imaging". At the timing t207, the signal generator 104 generates a valid imaging synchronization signal.

At the timing t208 and the timing t209, the current first instruction information and the current second instruction information are "imaging/imaging", and the previous third instruction information is "imaging". At the timings, the third instruction information after updating is "imaging". At the timings, the signal generator 104 generates a valid imaging synchronization signal.

After the timing t209, the second instruction information is changed to "stopping". At this time, the current first instruction information and the current second instruction information are "imaging/stopping", and the previous third instruction information is "imaging". In this case, there is a possibility that the capsule endoscope 10 is stopped with respect to the human body, and the human body is moving. According to this, the information generator 103 sets the third instruction information to "stopping". At the timing t210, the imaging synchronization signal is invalid. According to this, unnecessary imaging is suppressed.

After the timing t210, the current first instruction information and the current second instruction information are "imaging/stopping", and the previous third instruction information is "stopping". In this case, there is a possibility that the capsule endoscope 10 is stopped with respect to the human body, and the human body is moving. However, the information generator 103 sets the third instruction information to "imaging". At the timing t211, the signal generator 104 generates a valid imaging synchronization signal. According to this, imaging is performed by the imager 105, and an image is acquired. The second analyzer 102 can confirm whether or not the capsule endoscope 10 is moving with respect to the human body on the basis of the image.

In the third operation, when the current first instruction information and the current second instruction information are "imaging/stopping", and the previous third instruction information is "imaging", the third instruction information is set to "stopping", and thus unnecessary imaging is suppressed. As a result, power consumption of the capsule endoscope 10 is reduced. When the current first instruction information and the current second instruction information are "imaging/stopping", and the previous third instruction information is "stopping", the third instruction information is set to "imaging". According to this, an image, which is used to confirm whether or not the capsule endoscope 10 is moving with respect to the human body is acquired.

Fourth Operation

In a fourth operation, the information generator 103 generates the third instruction information on the basis of current first instruction information, current second instruction information, previous first instruction information, and previous second instruction information. FIG. 7 shows state information in the fourth operation. In FIG. 7, the state information is shown as a table. A current first instruction information state, a current second instruction information state, a previous first instruction information state, a previous second instruction information state, and a third instruction information state are correlated with each other. Respective pieces of instruction information represent any one value between two values. The two values include "imaging" and "stopping".

The current first instruction information state and the current second instruction information state, and the third instruction information corresponding thereto are described in the same row. The previous first instruction information state and the previous second instruction information state, and the third instruction information corresponding thereto are described in the same column. For example, in a case in which the current first instruction information and the current second instruction information are "stopping/imaging", and the previous first instruction information and the previous second instruction information are "stopping/imaging", the third instruction information generated by the information generator 103 is "stopping".

The third instruction information state in a column C11 and a column C12 in the table shown in FIG. 7 is the same as a state in a case in which the previous first instruction information is "stopping" in the table shown in FIG. 2. The third instruction information state in a column C13 in the table shown in FIG. 7 is the same as a state in a case in which the previous first instruction information is "imaging" in the table shown in FIG. 2. The third instruction information state in a column C14 in the table shown in FIG. 7 is the same as a state in a case in which the previous first instruction information is "imaging" in the table shown in FIG. 2 except for a case in which the current first instruction information and the current second instruction information are "stopping/imaging".

In a case in which the current first instruction information and the current second instruction information are "stopping/imaging" and the previous first instruction information and the previous second instruction information are "imaging/imaging", movement detected by the sensor 100 is greatly reduced, and movement detected from an image is large. In this case, there is a possibility that the capsule endoscope 10 that is moving may terminate movement.

However, the third instruction information is set to "imaging" to confirm whether or not the capsule endoscope 10 is moving by an image.

In the fourth operation, in a case in which the current first instruction information and the current second instruction information represent a relatively low imaging frequency ("stopping"), the third instruction information represents a relatively low imaging frequency ("stopping"). In a case in which the current first instruction information represents a relatively low imaging frequency ("stopping") and the current second instruction information represents a relatively high imaging frequency ("imaging"), the third instruction information is based on the previous first instruction information and the previous second instruction information. In a case in which the current first instruction information represents a relatively low imaging frequency ("stopping") and the current second instruction information represents a relatively high imaging frequency ("imaging"), the third instruction information represents a relatively high imaging frequency ("imaging") only when the previous first instruction information and the previous second instruction information represent a relatively high imaging frequency ("imaging"). In a case in which the current first instruction information represents a relatively high imaging frequency ("imaging") and the current second instruction information represents a relatively low imaging frequency ("stopping"), the third instruction information is based on the previous first instruction information. In a case in which the current first instruction information represents a relatively high imaging frequency ("imaging"), the current second instruction information represents a relatively low imaging frequency ("stopping"), and the previous first instruction information represents a relatively low imaging frequency ("stopping"), the third instruction information represents a relatively high imaging frequency ("imaging"). In a case in which the current first instruction information represents a relatively high imaging frequency ("imaging"), the current second instruction information represents a relatively low imaging frequency ("stopping"), and the previous first instruction information represents a relatively high imaging frequency ("imaging"), the third instruction information represents a relatively low imaging frequency ("stopping"). In a case in which the current first instruction information and the current second instruction information represent a relatively high imaging frequency ("imaging"), the third instruction information represents a relatively high imaging frequency ("imaging").

The information generator 103 generates the third instruction information on the basis of the state information. In the state information, the first instruction information and the second instruction information at a first time point, the first instruction information and the second instruction information at a second time point, and the third instruction information to be generated are correlated with each other. In the state information shown in FIG. 7, the number of pieces of the third instruction information that causes an imaging frequency to become relatively low is greater than the number of pieces of the third instruction information that causes the imaging frequency to become relatively high. A third instruction information state in which the imaging frequency becomes relatively low is "stopping". A third instruction information state in which the imaging frequency becomes relatively high is "imaging". The number of pieces of the third instruction information set to "stopping" is 9. The number of pieces of the third instruction information set to "imaging" is 7. According to this, as a whole, the effect of suppressing unnecessary imaging is likely to be higher than the effect of suppressing failure of imaging the test subject. The same effect can be obtained in the first to third operations.

FIG. 8 shows the fourth operation of the capsule endoscope 10. In FIG. 8, the first instruction information state, the second instruction information state, the third instruction information state, and a waveform of the imaging synchronization signal are shown. With regard to the imaging synchronization signal, a vertical direction in FIG. 8 represents a voltage. Time proceeds to the right in FIG. 8.

An operation relating to a timing t301 to a timing t304 is the same as the operation relating to the timing t101 to the timing t104 in the first operation shown in FIG. 3.

After the timing t304, the first instruction information is changed to "stopping". At this time, the current first instruction information and the current second instruction information are "stopping/imaging", and the previous first instruction information and the previous second instruction information are "imaging/imaging". In this case, there is a possibility that the capsule endoscope 10 that is moving may terminate movement. However, the information generator 103 sets the third instruction information to "imaging". At a timing t305, the signal generator 104 generates a valid imaging synchronization signal. According to this, imaging is performed by the imager 105, and an image is acquired. The second analyzer 102 can confirm whether or not the capsule endoscope 10 is moving on the basis of the image.

After the timing t305, the current first instruction information and the current second instruction information are "stopping/imaging", and the previous first instruction information and the previous second instruction information are "stopping/imaging". In this case, there is a high possibility that the capsule endoscope 10 that is moving may terminate movement. According to this, the information generator 103 sets the third instruction information to "stopping". At the timing t306, the imaging synchronization signal is invalid. According to this, unnecessary imaging is suppressed.

An operation relating to a timing t307 to a timing t311 is the same as the operation relating to the timing t107 to the timing t111 in the first operation shown in FIG. 3.

In the fourth operation, when the first instruction information is changed from "stopping" to "imaging", the third instruction information is set to "imaging", and thus failure of imaging the test subject is suppressed. When the first instruction information is continuously "imaging" and the second instruction information is "stopping", the third instruction information is set to "stopping", and thus unnecessary imaging is suppressed. As a result, power consumption of the capsule endoscope 10 is reduced. When the second instruction information is continuously "imaging", and the first instruction information is changed from "imaging" to "stopping", the third instruction information is set to "imaging". According to this, an image, which is used to confirm whether or not the capsule endoscope 10 is moving is acquired.

In the fourth operation, there are many cases in which the imaging frequency becomes relatively low. According to this, unnecessary imaging is likely to be suppressed.

Fifth Operation

In a fifth operation, the information generator 103 retains the generated third instruction information regardless of contents of the first instruction information until the second instruction information is generated.

In a case in which the imager 105 performs imaging, the second analyzer 102 updates the second instruction information on the basis of an image output from the imager 105. For example, the information generator 103 updates the third instruction information at an interval of a first time. The second analyzer 102 updates the second instruction information before an updating timing of the third instruction information occurs after the imager 105 performs imaging. However, delay and the like occur in image processing by the second analyzer 102. In this case, there is a possibility that the second instruction information is not updated before the updating timing of the third instruction information occurs. According to this, the information generator 103 retains the generated third instruction information regardless of contents of the first instruction information until the second instruction information is updated.

For example, in a case in which the second instruction information is not output from the second analyzer 102 before passage of a predetermined time from a time point at which the imager 105 performs imaging, the information generator 103 retains the generated third instruction information regardless of contents of the first instruction information. In a case in which the second instruction information is output from the second analyzer 102 before passage of the predetermined time from the time point at which the imager 105 performs imaging, the information generator 103 generates the third instruction information on the basis of state information. The predetermined time is based on an updating interval of the third instruction information by the information generator 103.

FIG. 9 shows the fifth operation of the capsule endoscope 10. In FIG. 9, a first instruction information state, a second instruction information state, a third instruction information state, and a waveform of the imaging synchronization signal are shown. With regard to the imaging synchronization signal, a vertical direction in FIG. 9 represents a voltage. Time proceeds to the right in FIG. 9. With respect to a case in which state information in the fifth operation is the same as state information in the fourth operation, the fifth operation will be described.

At a timing t401, the first instruction information, the second instruction information, and the third instruction information are "stopping", and the imaging synchronization signal is invalid.

After the timing t401, the first instruction information is changed to "imaging". At this time, the current first instruction information and the current second instruction information are "imaging/stopping", and the previous first instruction information and the previous second instruction information are "stopping/stopping". According to this, the information generator 103 sets the third instruction information to "imaging". At a timing t402, the signal generator 104 generates a valid imaging synchronization signal.

At the timing t402, the imaging synchronization signal becomes valid, and thus the imager 105 performs imaging. The second instruction information is not updated before the updating timing of the third instruction information occurs, and thus the information generator 103 retains the third instruction information. That is, the information generator 103 sets the third instruction information to "imaging". At a timing t403, the signal generator 104 generates a valid imaging synchronization signal.

At the timing t403, the imaging synchronization signal becomes valid, and thus the imager 105 performs imaging. The second instruction information is updated before the updating timing of the third instruction information occurs. According to this, the information generator 103 generates the third instruction information on the basis of the state information. When the second instruction information is updated, the current first instruction information and the current second instruction information are "imaging/imaging", and the previous first instruction information and the previous second instruction information are "imaging/stopping". According to this, the information generator 103 sets the third instruction information to "imaging". At a timing t404, the signal generator 104 generates a valid imaging synchronization signal.

At the timing t404, the imaging synchronization signal becomes valid, and thus the imager 105 performs imaging. The second instruction information is not updated before the updating timing of the third instruction information occurs, and thus the information generator 103 retains the third instruction information. That is, the information generator 103 sets the third instruction information to "imaging". At a timing t405, the signal generator 104 generates a valid imaging synchronization signal.

At the timing t405, the imaging synchronization signal becomes valid, and thus the imager 105 performs imaging. The second instruction information is updated before the updating timing of the third instruction information occurs. According to this, the information generator 103 generates the third instruction information on the basis of the state information. When the second instruction information is updated, the current first instruction information and the current second instruction information are "imaging/stopping", and the previous first instruction information and the previous second instruction information are "imaging/imaging". According to this, the information generator 103 sets the third instruction information to "stopping". At a timing t406, the imaging synchronization signal is invalid.

After the timing t406, the current first instruction information and the current second instruction information are "imaging/stopping", and the previous first instruction information and the previous second instruction information are "imaging/stopping". According to this, the information generator 103 sets the third instruction information to "stopping". At a timing t407, the imaging synchronization signal is invalid.

After the timing t407, the first instruction information is changed to "stopping". At this time, the current first instruction information and the current second instruction information are "stopping/stopping", and the previous first instruction information and the previous second instruction information are "imaging/stopping". According to this, the information generator 103 sets the third instruction information to "stopping". At a timing t408, the imaging synchronization signal is invalid.

In the fifth operation, in a case in which the second instruction information is not updated before the updating timing of the third instruction information occurs, the third instruction information is retained regardless of contents of the first instruction information. According to this, the capsule endoscope 10 can retain a previous control result until the second instruction information is updated.

Sixth Operation

In a sixth operation, the information generator 103 generates the third instruction information on the basis of the current first instruction information, the current second instruction information, the previous first instruction information, and the previous second instruction information. FIG. 10 shows state information in the sixth operation. In FIG. 10, the state information is shown as a table. A current first instruction information state, a current second instruction information state, a previous first instruction information state, a previous second instruction information state, and a third instruction information state are correlated with each other. Respective pieces of instruction information represent any one value between two values. The two values include "imaging" and "stopping".

The current first instruction information state and the current second instruction information state, and the third instruction information corresponding thereto are described in the same row. The previous first instruction information state and the previous second instruction information state, and the third instruction information corresponding thereto are described in the same column. For example, in a case in which the current first instruction information and the current second instruction information are "stopping/imaging", and the previous first instruction information and the previous second instruction information are "stopping/imaging", the third instruction information generated by the information generator 103 is "imaging".

The third instruction information state in a column C21 and a column C22 in the table shown in FIG. 10 is the same as a state in a case in which the previous first instruction information is "stopping" in the table shown in FIG. 2 except for a case in which the current first instruction information and the current second instruction information are "stopping/imaging". The third instruction information state in a column C23 in the table shown in FIG. 10 is the same as a state in a case in which the previous second instruction information in the table shown in FIG. 4 is "stopping" except for a case in which the current first instruction information and the current second instruction information are "stopping/imaging". The third instruction information state in a column C24 in the table shown in FIG. 10 is the same as a state in a case in which the previous second instruction information is "imaging" in the table shown in FIG. 4 except for a case in which the current first instruction information and the current second instruction information are "stopping/imaging".

In a case in which the current first instruction information and the current second instruction information are "stopping/imaging", movement detected by the sensor 100 is small, and movement detected from an image is large. In this case, there is a possibility that the capsule endoscope 10 is stopped. However, the third instruction information is set to "imaging" to confirm whether or not the capsule endoscope 10 is moving by an image.

In the sixth operation, in a case in which the current first instruction information and the current second instruction information represent a relatively low imaging frequency ("stopping"), the third instruction information represents a relatively low imaging frequency ("stopping"). In a case in which the current first instruction information represents a relatively low imaging frequency ("stopping"), and the current second instruction information represents a relatively high imaging frequency ("imaging"), the third instruction information represents a relatively high imaging frequency ("imaging"). In a case in which the current first instruction information represents a relatively high imaging frequency ("imaging"), and the current second instruction information represents a relatively low imaging frequency ("stopping"), the third instruction information is based on the previous first instruction information and the previous second instruction information. In a case in which the current first instruction information represents a relatively high imaging frequency ("imaging"), and the current second instruction information represents a relatively low imaging frequency ("stopping"), the third instruction information represents a relatively low imaging frequency ("stopping") only when the previous first instruction information and the previous second instruction information represent a relatively high imaging frequency ("imaging"). In a case in which the current first instruction information and the current second instruction information represent a relatively high imaging frequency ("imaging"), the third instruction information represents a relatively high imaging frequency ("imaging").

The information generator 103 generates the third instruction information on the basis of the state information. In the state information, the first instruction information and the second instruction information at a first time point, the first instruction information and the second instruction information at a second time point, and the third instruction information to be generated are correlated with each other. In the state information shown in FIG. 10, the number of pieces of the third instruction information that causes an imaging frequency to become relatively high is greater than the number of pieces of the third instruction information that causes the imaging frequency to become relatively low. A third instruction information state in which the imaging frequency becomes relatively high is "imaging". A third instruction information state in which the imaging frequency becomes relatively low is "stopping". The number of pieces of the third instruction information set to "imaging" is 11. The number of pieces of the third instruction information set to "stopping" is 5. According to this, as a whole, the effect of suppressing failure of imaging the test subject is likely to be higher than the effect of suppressing unnecessary imaging.

FIG. 11 shows the sixth operation of the capsule endoscope 10. In FIG. 11, a first instruction information state, a second instruction information state, a third instruction information state, and a waveform of the imaging synchronization signal are shown. With regard to the imaging synchronization signal, a vertical direction in FIG. 11 represents a voltage. Time proceeds to the right in FIG. 11.

At a timing t501, the first instruction information, the second instruction information, and the third instruction information are "stopping", and the imaging synchronization signal is invalid.

After the timing t501, the first instruction information is changed to "imaging". At this time, the current first instruction information and the current second instruction information are "imaging/stopping", and the previous first instruction information and the previous second instruction information are "stopping/stopping". In this case, there is a possibility that the capsule endoscope 10 that is stopped may initiate movement. According to this, the information generator 103 sets the third instruction information to "imaging". At a timing t502, the signal generator 104 generates a valid imaging synchronization signal. Accordingly, failure of imaging the test subject is suppressed.

After the timing t502, the second instruction information is changed to "imaging". At this time, the current first instruction information and the current second instruction information are "imaging/imaging", and the previous first instruction information and the previous second instruction information are "imaging/stopping". According to this, the information generator 103 sets the third instruction information to "imaging". At a timing t503, the signal generator 104 generates a valid imaging synchronization signal.

After the timing t503, the current first instruction information and the current second instruction information are "imaging/imaging", and the previous first instruction information and the previous second instruction information are "imaging/imaging". According to this, the information generator 103 sets the third instruction information to "imaging". At a timing t504, the signal generator 104 generates a valid imaging synchronization signal.

At a timing t505, respective pieces of instruction information are the same as respective pieces of instruction information at the timing t504. At the timing t505, the signal generator 104 generates a valid imaging synchronization signal.

After the timing t505, the first instruction information is changed to "stopping". At this time, the current first instruction information and the current second instruction information are "stopping/imaging", and the previous first instruction information and the previous second instruction information are "imaging/imaging". According to this, the information generator 103 sets the third instruction information to "imaging". At a timing t506, the signal generator 104 generates a valid imaging synchronization signal. At the timing t506, movement detected by the sensor 100 is small, but movement detected from an image is large. According to this, imaging is continuously performed. Imaging is performed by the imager 105, and an image is acquired. The second analyzer 102 can confirm whether or not the capsule endoscope 10 is moving with respect to the human body on the basis of the image.

After the timing t506, the second instruction information is changed to "stopping". At this time, the current first instruction information and the current second instruction information are "stopping/stopping", and the previous first instruction information and the previous second instruction information are "stopping/imaging". According to this, the information generator 103 sets the third instruction information to "stopping". At a timing t507, the imaging synchronization signal is invalid. Since movement detected from an image becomes small, it is detected that the capsule endoscope 10 is reliably stopped.

After the timing t507, the current first instruction information and the current second instruction information are "stopping/stopping", and the previous first instruction information and the previous second instruction information are "stopping/stopping". According to this, the information generator 103 sets the third instruction information to "stopping". At a timing t508, the imaging synchronization signal is invalid.

In the sixth operation, there are many cases in which the imaging frequency becomes relatively high. According to this, failure of imaging the test subject is likely to be suppressed.

In the capsule endoscope 10 according to the first embodiment, the information generator 103 generates the third instruction information on the basis of the first instruction information and the second instruction information, and the signal generator 104 generates the imaging synchronization signal on the basis of the third instruction information. According to this, the capsule endoscope 10 can determine an imaging timing with high accuracy on the basis of data that is acquired by two sensors provided in the capsule endoscope 10, that is, the sensor 100 and the imager 105.

Modification Example of First Embodiment

Figure 12:
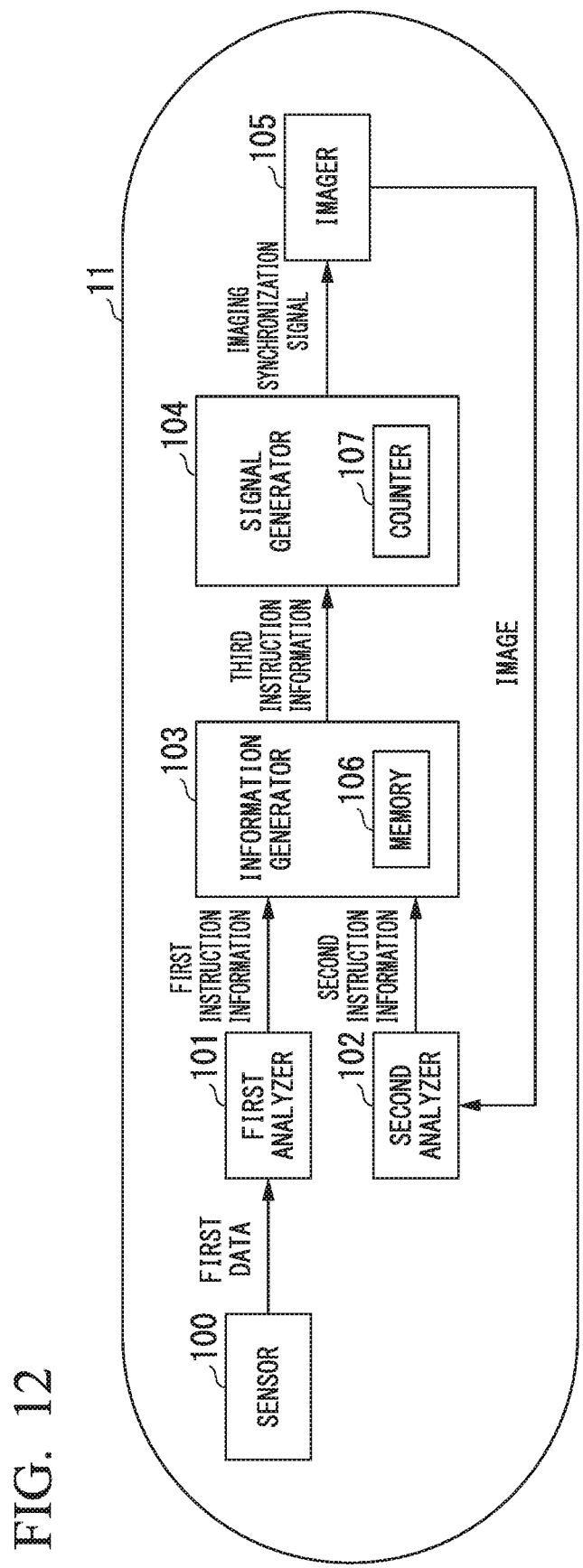
FIG. 12 is a block diagram showing a configuration of a capsule endoscope according to a modification example of the first embodiment of the present invention.

FIG. 12 shows a configuration of a capsule endoscope 11 according to a first modification example of the first embodiment of the present invention. With regard to the configuration shown in FIG. 12, description will be given of a difference from the configuration shown in FIG. 1.

The signal generator 104 includes a counter 107. A count value of the counter 107 increases or decreases from a reference value. The count value is calculated on the basis of the third instruction information each time the first instruction information is updated. When the imaging synchronization signal is generated, the count value becomes the reference value. When the count value increases from the reference value and the count value becomes equal to or greater than a predetermined value, or when the count value decreases from the reference value and the count value becomes equal to or less than the predetermined value, the signal generator 104 generates the imaging synchronization signal.

The counter 107 is provided in the signal generator 104. The counter 107 may be provided independently from the signal generator 104. The counter 107 performs count on the basis of the third instruction information. The counter 107 can perform at least one of up-counting and down-counting. The count value of the counter 107 is set to the reference value when the count is initiated. The count value increases or decreases from the reference value due to the counting. When the imaging synchronization signal is generated, the count value is set again to the reference value. The reference value is not limited to a constant value. The counting by the counter 107 is performed at an interval of a first time. That is, the count value increases or decreases in synchronization with generation of the first instruction information by the first analyzer 101. An operation of the counter 107 need not synchronize with the generation of the first instruction information by the first analyzer 101.

The reference value may include a first reference value and a second reference value. The second reference value may be the same as or different from the first reference value. When the first reference value is smaller than a first predetermined value, and the count value increases from the first reference value, and the count value becomes equal to or greater than the first predetermined value, the count value becomes the second reference value that is smaller than the first predetermined value. When the first reference value is greater than the first predetermined value, and the count value decreases from the first reference value, and the count value becomes equal to or less than the first predetermined value, the count value becomes the second reference value that is greater than the first predetermined value.

With regard to a configuration other than the above-described configuration, the configuration shown in FIG. 12 is the same as the configuration shown in FIG. 1.

FIG. 13 shows state information in the modification example of the first embodiment. In FIG. 13, the state information is shown as a table. A current first instruction information state, a current second instruction information state, a previous first instruction information state, a previous second instruction information state, and a third instruction information state are correlated with each other. The first instruction information and the third instruction information show any one value among three values. The three values, which can be represented by the first instruction information and the third instruction information, include "H", "M", and "L". "H" corresponds to a case in which movement of the capsule endoscope 11 is large. "M" corresponds to a case in which movement of the capsule endoscope 11 is intermediate. "L" corresponds to a case in which movement of the capsule endoscope 11 is small. The second instruction information represents any one value between two values. The two values, which can be represented by the second instruction information, include "H" and "M". "H" corresponds to a case in which movement of the capsule endoscope 11 is large. "M" corresponds to a case in which movement of the capsule endoscope 11 is small or movement of the capsule endoscope 11 is intermediate. As in the first instruction information and the third instruction information, the second instruction information may represent any one value among the three values.

The current first instruction information state and the current second instruction information state, and the third instruction information corresponding thereto are described in the same row. The previous second instruction information state and the third instruction information corresponding thereto are described in the same column. For example, in a case in which the current first instruction information and the current second instruction information are "L/H", and the previous first instruction information and the previous second instruction information are "L/H", the third instruction information generated by the information generator 103 is "L".

In a case in which the current first instruction information is "L", movement detected by the sensor 100 is small. That is, there is a high possibility that the capsule endoscope 11 is stopped. In this case, the third instruction information is set to "L". Similarly, in a case in which the current first instruction information is "M", movement detected by the sensor 100 is intermediate. That is, there is a high possibility that the capsule endoscope 11 is slowly moving. In this case, the third instruction information is set to "M".

In a case in which the current first instruction information is "H", movement detected by the sensor 100 is large. That is, there is a high possibility that the capsule endoscope 11 is moving. In this case, the third instruction information is set to "H" except for some cases. In a case in which the current first instruction information and the current second instruction information are "H/M", and the previous first instruction information and the previous second instruction information are "H/H", movement detected by the sensor 100 is large, and movement detected from an image decreases. In this case, there is a possibility that the capsule endoscope 11 is stopped with respect to the human body, and the human body is moving. Accordingly, the third instruction information is set to "M" to suppress unnecessary imaging. In a case in which the current first instruction information and the current second instruction information are "H/M", and the previous first instruction information and the previous second instruction information are "H/M", the third instruction information is retained to a value that is previously set.

Figure 14:
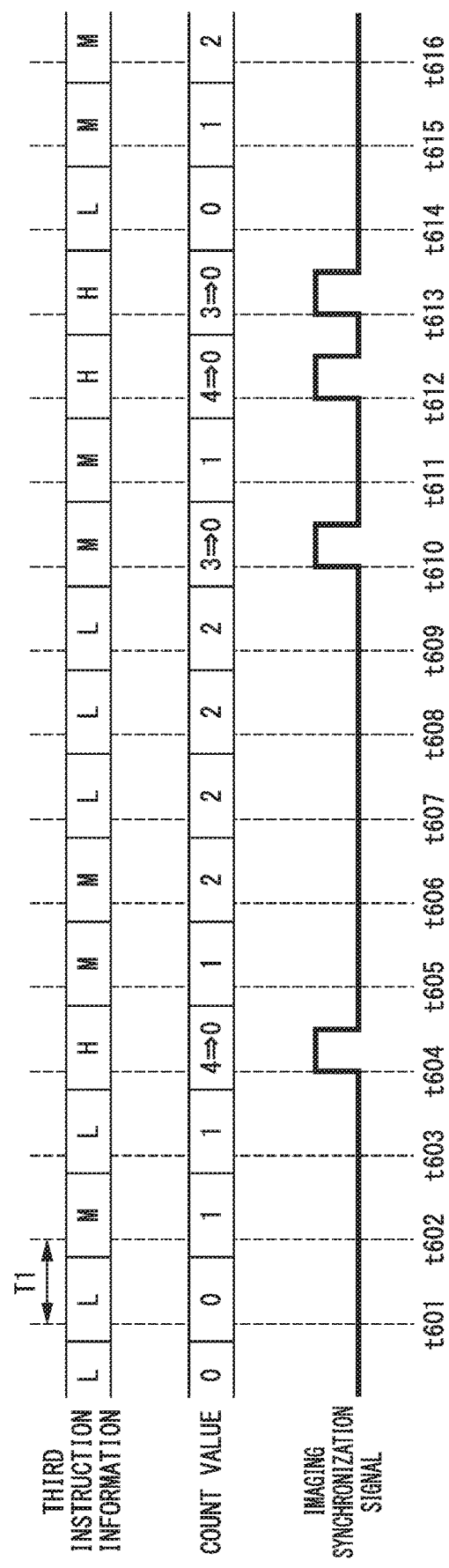
FIG. 14 is a timing chart showing an operation of the capsule endoscope according to the modification example of the first embodiment of the present invention.

FIG. 14 shows the operation of the capsule endoscope 11. In FIG. 14, the third instruction information state, the count value, and a waveform of the imaging synchronization signal are shown. With regard to the imaging synchronization signal, a vertical direction in FIG. 14 represents a voltage. Time proceeds to the right in FIG. 14. In FIG. 14, the first instruction information and the second instruction information are omitted.

The count value increases from the reference value. When the count value becomes equal to or greater than the first predetermined value, the signal generator 104 generates the imaging synchronization signal. The count value increases in synchronization with generation of the third instruction information by the information generator 103. A value corresponding to the third instruction information is added to the count value in synchronization with generation of the third instruction information by the information generator 103. The reference value is a second predetermined value different from the first predetermined value.

The counter 107 counts the value corresponding to the third instruction information, and generates the count value. The counter 107 generates the count value for every first time T1. In a case in which the third instruction information is "H", "3" is added to the count value. In a case in which the third instruction information is "M", "1" is added to the count value. In a case in which the third instruction information is "L", "0" is added to the count value. When the count value becomes equal to or greater than the first predetermined value, the count value is changed to the reference value. The reference value is 0. The first predetermined value is 3.

A period for which the signal generator 104 refers to the count value is constant. The signal generator 104 refers to the count value at an interval of the first time T1. The signal generator 104 generates the imaging synchronization signal based on the count value. In a case in which the count value is equal to or greater than the first predetermined value, the signal generator 104 generates the imaging synchronization signal.

At a timing t601, the third instruction information is "L". At the timing t601, "0" is added to the count value. At this time, the count value is 0. At this time, the count value is less than 3 that is the first predetermined value. According to this, at the timing t601, the imaging synchronization signal is invalid.

At a timing t602, the third instruction information is "M". At the timing t602, "1" is added to the count value, and thus the count value is changed to 1. At this time, the count value is less than 3 that is the first predetermined value. According to this, at the timing t602, the imaging synchronization signal is invalid.

At a timing t603, the third instruction information is "L". At the timing t603, "0" is added to the count value. At this time, the count value is 1. At this time, the count value is less than 3 that is the first predetermined value. According to this, at the timing t603, the imaging synchronization signal is invalid.

At a timing t604, the third instruction information is "H". At the timing t604, "3" is added to the count value, and thus the count value is changed to 4. At this time, the count value is equal to or greater than 3 that is the first predetermined value. According to this, at the timing t604, the signal generator 104 generates a valid imaging synchronization signal. At the timing t604, the count value is changed to 0 that is the reference value.

At a timing t605 and a timing t606, the third instruction information is "M". At the timing t605 and the timing t606, "1" is added to the count value. At the timing t605, the count value is changed to 1, and at the timing t606, the count value is changed to 2. At the timing t605 and the timing t606, the count value is less than 3 that is the first predetermined value. According to this, at the timing t605 and the timing t606, the imaging synchronization signal is invalid.

At a timing t607, a timing t608, and a timing t609, the third instruction information is "L". At the timing t607, the timing t608, and the timing t609, "0" is added to the count value. At this time, the count value is 2. At this time, the count value is less than 3 that is the first predetermined value. According to this, at the timing t607, the timing t608, and the timing t609, the imaging synchronization signal is invalid.

At a timing t610, the third instruction information is "M". At the timing t610, "1" is added to the count value, and thus the count value is changed to 3. At this time, the count value is equal to or greater than 3 that is the first predetermined value. According to this, at the timing t610, the signal generator 104 generates a valid imaging synchronization signal. At the timing t610, the count value is changed to 0 that is the reference value.

Detailed description of the operation at a period from a timing t611 to a timing t616 will be omitted. At the timing t612 and the timing t613, the imaging synchronization signal is valid. At the timing t611, the timing t614, the timing t615, and the timing t616, the imaging synchronization signal is invalid.

Values which are added to the count value in correspondence with respective states of the third instruction information are not limited to the above-described values. The reference value and the predetermined value are not limited to the above-described values.

The value corresponding to the third instruction information may be subtracted from the count value in synchronization with generation of the third instruction information by the information generator 103. In this case, when the count value becomes equal to or less than the first predetermined value, the signal generator 104 generates the imaging synchronization signal.

In the modification example of the first embodiment, a method of generating the imaging synchronization signal from the third instruction information is not limited to the above-described method. In the modification example of the first embodiment, at least one of the first instruction information and the second instruction information may represent any one value among three or more values. The third instruction information may represent at least one value among the three or more values.

In the modification example of the first embodiment, when the number of instruction information states increases, a more reliable imaging synchronization signal with respect to movement of the capsule endoscope 11 is generated.

Second Embodiment

Figure 15:
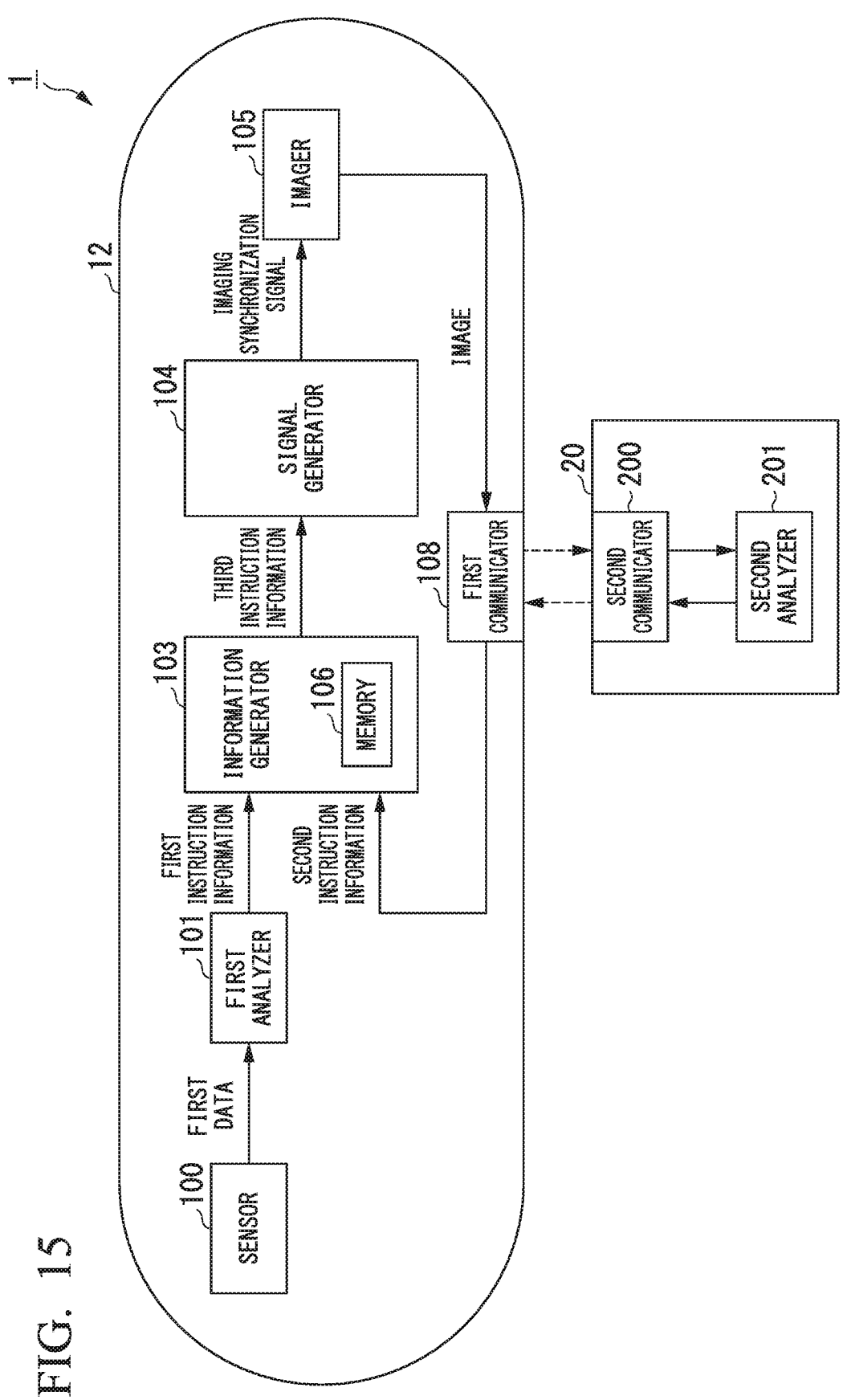
FIG. 15 is a block diagram showing a configuration of a capsule endoscope system according to a second embodiment of the present invention.

FIG. 15 shows a configuration of a capsule endoscope system 1 according to a second embodiment of the present invention. As shown in FIG. 15, the capsule endoscope system 1 includes a capsule endoscope 12 and a radio communication device 20.

With regard to a configuration of the capsule endoscope 12, description will be given of a difference from the configuration of the capsule endoscope 10 shown in FIG. 1. The capsule endoscope 12 does not include the second analyzer 102. The capsule endoscope 12 includes a first communicator 108 that performs radio communication with the radio communication device 20. The first communicator 108 is a radio communication circuit (radio communication device). The first communicator 108 transmits an image that is second data to the radio communication device 20. The first communicator 108 receives the second instruction information from the radio communication device 20. The first communicator 108 outputs the second instruction information to the information generator 103. The configuration of the capsule endoscope 12 is the same as the configuration of the capsule endoscope 10 except for the above-described configuration.

The radio communication device 20 includes a second communicator 200 and a second analyzer 201. The second communicator 200 is a radio communication circuit (radio communication device). The second communicator 200 performs radio communication with the capsule endoscope 12. The second communicator 200 receives an image that is second data from the capsule endoscope 12. The second communicator 200 outputs the image to the second analyzer 201. The second communicator 200 transmits the second instruction information to the capsule endoscope 12.

The second analyzer 201 is constituted by one or a plurality of processors. The second analyzer 201 performs the same processing as in the second analyzer 102 according to the first embodiment. The second analyzer 201 analyzes the second data and generates the second instruction information that represents the analysis result. The second analyzer 201 outputs the second instruction information to the second communicator 200.

The operation of the information generator 103 and the signal generator 104 is the same as the operation in the first embodiment. The capsule endoscope 12 may include the counter 107 shown in FIG. 12.

In the capsule endoscope 12 according to the second embodiment, the information generator 103 generates the third instruction information on the basis of the first instruction information and the second instruction information, and the signal generator 104 generates the imaging synchronization signal on the basis of the third instruction information. According to this, the capsule endoscope 12 can determine an imaging timing with high accuracy on the basis of data that is acquired by the two sensors provided in the capsule endoscope 12, that is, the sensor 100 and the imager 105.

Modification Example of Second Embodiment

Figure 16:
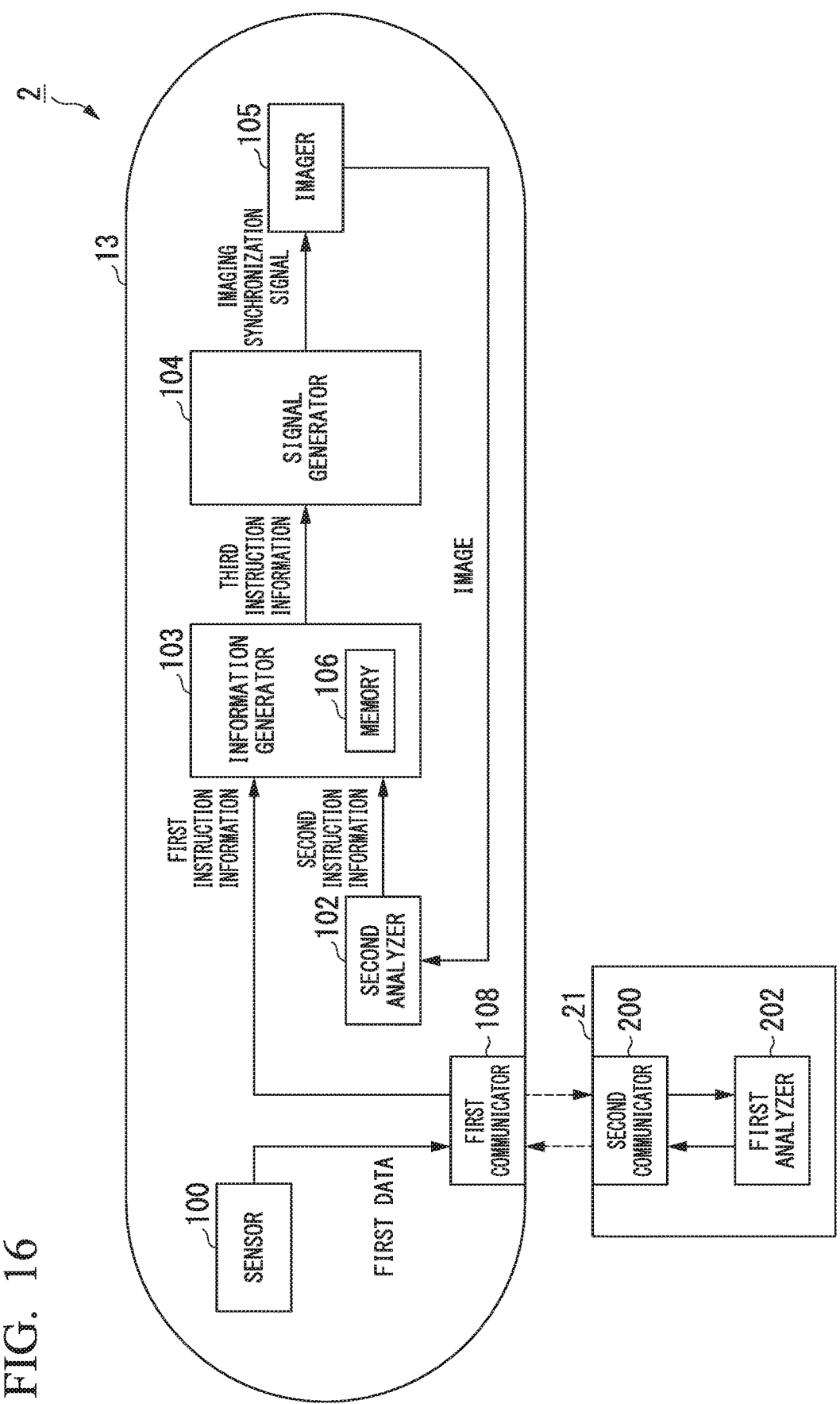
FIG. 16 is a block diagram showing a configuration of a capsule endoscope system according to a modification example of the second embodiment of the present invention.

FIG. 16 shows a configuration of a capsule endoscope system 2 according to a modification example of the second embodiment of the present invention. As shown in FIG. 16, the capsule endoscope system 2 includes a capsule endoscope 13 and a radio communication device 21.

With regard to a configuration of the capsule endoscope 13, description will be given of a difference from the configuration of the capsule endoscope 10 shown in FIG. 1. The capsule endoscope 13 does not include the first analyzer 101. The capsule endoscope 13 includes the first communicator 108 that performs radio communication with the radio communication device 21. The first communicator 108 transmits first data to the radio communication device 21. The first communicator 108 receives the first instruction information from the radio communication device 21. The first communicator 108 outputs the first instruction information to the information generator 103. The configuration of the capsule endoscope 13 is the same as the configuration of the capsule endoscope 10 except for the above-described configuration.

With regard to the configuration of the radio communication device 21, description will be given of a difference from the configuration of the radio communication device 20 shown in FIG. 15. The radio communication device 21 includes a first analyzer 202 instead of the second analyzer 201 shown in FIG. 15. The second communicator 200 receives first data from the capsule endoscope 13. The second communicator 200 outputs the first data to the first analyzer 202. The second communicator 200 transmits the first instruction information to the capsule endoscope 13.

The first analyzer 202 is constituted by one or a plurality of processors. The first analyzer 202 performs the same processing as in the first analyzer 101 according to the first embodiment. The first analyzer 202 analyzes the first data and generates the first instruction information that represents the analysis result. The first analyzer 202 outputs the first instruction information to the second communicator 200. The configuration of the radio communication device 21 is the same as the configuration of the radio communication device 20 except for the above-described configuration.

The operation of the information generator 103 and the signal generator 104 is the same as in the first embodiment. The capsule endoscope 13 may include the counter 107 shown in FIG. 12.

The capsule endoscope 13 need not include the second analyzer 102, and the radio communication device 21 may further include the second analyzer 201. In this case, the first communicator 108 transmits the first data and the image to the radio communication device 21. The first communicator 108 receives the first instruction information and the second instruction information from the radio communication device 21. The second communicator 200 receives the first data and the image from the capsule endoscope 13. The second communicator 200 transmits the first instruction information and the second instruction information to the capsule endoscope 13.

In the respective embodiments of the present invention, the third instruction information may be generated on the basis of any one of the current first instruction information and the current second instruction information, and at least two among the previous first instruction information to the previous third instruction information. The third instruction information state corresponding to the current instruction information and the previous instruction information is not limited to the example shown in the respective embodiments. The third instruction information state that is generated can be freely changed in correspondence with an operation that is assumed, and the like. A previous time point, at which the instruction information which is referenced during generation of the third instruction information is generated, may be a time point previous from a time point, at which the third instruction information is to be generated, by a time longer than the first time.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A capsule endoscope comprising:
a first sensor configured to generate first data representing a movement of the capsule endoscope at a first time in an examination and first data representing a movement of the capsule endoscope at a second time in the examination prior to the first time;
an image sensor configured to generate second data comprising an image acquired by the image sensor in the examination in response to an image synchronization signal; and
one or more processors comprising hardware, wherein the one or more processors are configured to:
generate a first instruction information for the second time instructing one of increasing an imaging frequency and decreasing the imaging frequency based on the first data at the second time;
generate a second instruction information for the second time instructing one of increasing the imaging frequency and decreasing the imaging frequency based on the second data generated at the second time or a time prior to the second time;
generate a third instruction information instructing whether or not to generate the image synchronization signal for the image sensor after the second time;
generate a first instruction information for the first time instructing one of increasing the imaging frequency and decreasing the imaging frequency based on the first data at the first time;
generate a second instruction information for the first time instructing one of increasing the imaging frequency and decreasing the imaging frequency based on the second data at the first time or a time prior to the first time; and
generate a third instruction information instructing whether or not to generate an image synchronization signal for the image sensor after the first time, based on:
the first instruction information for the first time;
the second instruction information for the first time; and
any one of the first instruction information for the second time, the second instruction information for the second time and the third instruction information instructing whether or not to generate the image synchronization signal for the image sensor after the second time.

2. The capsule endoscope according to claim 1, wherein at least one of the first instruction information for the second time and for the first time and the second instruction information for the second time and for the first time represents any one of three or more types of values, and the third instruction information for the second time and for the first time represents any one of the three or more types of values.

3. The capsule endoscope according to claim 1, wherein the one or more processors are configured to:
increase or decrease a count value from a reference value,
wherein the count value is calculated on the basis of the third instruction information after the first time and after the second time each time the first instruction information is updated,
wherein the count value becomes the reference value in response to the image synchronization signal being generated, and
wherein in response to the count value increasing from the reference value and the count value becoming equal to or greater than a first predetermined value, or in response to the count value decreasing from the reference value and the count value becoming equal to or less than a second predetermined value, the one or more processors are configured to generate the imaging synchronization signal.

4. The capsule endoscope according to claim 1, wherein the one or more processors are configured to:
determine a possibility of a movement of the capsule endoscope with respect to a subject based on the first instruction information for the first time, the second instruction information for the first time and any one of the first instruction information for the second time, the second instruction information for the second time and the third instruction information instructing whether or not to generate the image synchronization signal for the image sensor after the second time; and
generate the third instruction information instructing whether or not to generate the image synchronization signal for the image sensor after the first time, based on the possibility of the movement of the capsule endoscope determined.

5. The capsule endoscope according to claim 1,
wherein the first instruction information for the second time and the first instruction information for the first time are updated at a first update interval from a first instruction information previously generated,
wherein the second instruction information for the second time and the second instruction information for the first time are updated at a second update interval from a second instruction information previously generated, and
wherein the first update interval is equal to or shorter than the second update interval.

6. The capsule endoscope according to claim 1,
wherein the one or more processors are configured to generate the third instruction information instructing to generate the image synchronization signal for the image sensor after the first time, based on:
the first instruction information for the first time instructing increasing the imaging frequency;
the second instruction information for the first time instructing decreasing the imaging frequency; and
any one of the first instruction information for the second time instructing decreasing the imaging frequency, the second instruction information for the second time decreasing the imaging frequency and the third instruction information instructing not to generate the image synchronization signal for the image sensor after the second time.

7. The capsule endoscope according to claim 1,
wherein the one or more processors are configured to generate the third instruction information instructing not to generate the image synchronization signal for the image sensor after the first time, based on:
the first instruction information for the first time instructing increasing the imaging frequency;
the second instruction information for the first time instructing decreasing the imaging frequency; and
any one of the first instruction information for the second time instructing increasing the imaging frequency, the second instruction information for the second time instructing increasing the imaging frequency and the third instruction information instructing to generate the image synchronization signal for the image sensor after the second time.

8. The capsule endoscope according to claim 1,
wherein the second time is a time point at which the third instruction information instructing whether or not to generate the image synchronization signal for the image sensor immediately before the first time at which the third instruction information instructing whether or not to generate the image synchronization signal for the image sensor.

9. A method for controlling a capsule endoscope comprising:
a first sensor configured to generate first data representing a movement of the capsule endoscope at a first time in an examination and first data representing a movement of the capsule endoscope at a second time in the examination prior to the first time; and
an image sensor configured to generate second data comprising an image acquired by the image sensor in the examination in response to an image synchronization signal,
wherein the method comprises:
generating a first instruction information for the second time instructing one of increasing an imaging frequency and decreasing the imaging frequency based on the first data at the second time;
generating a second instruction information for the second time instructing one of increasing the imaging frequency and decreasing the imaging frequency based on the second data generated at the second time or a time prior to the second time;
generating a third instruction information instructing whether or not to generate the image synchronization signal for the image sensor after the second time;
generating a first instruction information for the first time instructing one of increasing the imaging frequency and decreasing the imaging frequency based on the first data at the first time;
generating a second instruction information for the first time instructing one of increasing the imaging frequency and decreasing the imaging frequency based on the second data at the first time or a time prior to the first time; and
generating a third instruction information instructing whether or not to generate an image synchronization signal for the image sensor after the first time, based on:
the first instruction information for the first time;
the second instruction information for the first time; and
any one of the first instruction information for the second time, the second instruction information for the second time and the third instruction information instructing whether or not to generate the image synchronization signal for the image sensor after the second time.

10. The method according to claim 9, comprising:
determining a possibility of a movement of the capsule endoscope with respect to a subject based on the first instruction information for the first time, the second instruction information for the first time and any one of the first instruction information for the second time, the second instruction information for the second time and the third instruction information instructing whether or not to generate the image synchronization signal for the image sensor after the second time; and
generating the third instruction information instructing whether or not to generate the image synchronization signal for the image sensor after the first time, based on the possibility of the movement of the capsule endoscope determined.

11. The method according to claim 9,
wherein the first instruction information for the second time and the first instruction information for the first time are updated at a first update interval from a first instruction information previously generated,
wherein the second instruction information for the second time and the second instruction information for the first time are updated at a second update interval from a second instruction information previously generated, and
wherein the first update interval is equal to or shorter than the second update interval.

12. The method according to claim 9, comprising:
generating the third instruction information instructing to generate the image synchronization signal for the image sensor after the first time, based on:
the first instruction information for the first time instructing increasing the imaging frequency;
the second instruction information for the first time instructing decreasing the imaging frequency; and any one of the first instruction information for the second time instructing decreasing the imaging frequency, the second instruction information for the second time decreasing the imaging frequency and the third instruction information instructing not to generate the image synchronization signal for the image sensor after the second time.

13. The method according to claim 9, comprising:
generating the third instruction information instructing not to generate the image synchronization signal for the image sensor after the first time, based on:
the first instruction information for the first time instructing increasing the imaging frequency;
the second instruction information for the first time instructing decreasing the imaging frequency; and
any one of the first instruction information for the second time instructing increasing the imaging frequency, the second instruction information for the second time instructing increasing the imaging frequency and the third instruction information instructing to generate the image synchronization signal for the image sensor after the second time.

14. The method according to claim 9,
wherein the second time is a time point at which the third instruction information instructing whether or not to generate the image synchronization signal for the image sensor immediately before the first time at which the third instruction information instructing whether or not to generate the image synchronization signal for the image sensor.

15. A capsule endoscope system comprising:
a capsule endoscope comprising:
a first sensor configured to generate first data representing a movement of the capsule endoscope at a first time in an examination and first data representing a movement of the capsule endoscope at a second time in the examination prior to the first time;
an image sensor configured to generate second data comprising an image acquired by the image sensor in the examination in response to an image synchronization signal; and
one or more first processors comprising hardware; and
one or more second processors comprising hardware, wherein the one or more second processors are configured to:
generate a first instruction information for the second time instructing one of increasing an imaging frequency and decreasing the imaging frequency based on the first data at the second time;
generate a second instruction information for the second time instructing one of increasing the imaging frequency and decreasing the imaging frequency based on the second data generated at the second time or a time prior to the second time;
generate a first instruction information for the first time instructing one of increasing the imaging frequency and decreasing the imaging frequency based on the first data at the first time; and
generate a second instruction information for the first time instructing one of increasing the imaging frequency and decreasing the imaging frequency based on the second data at the first time or a time prior to the first time,
wherein the one or more first processors of the capsule endoscope are configured to:
generate a third instruction information instructing whether or not to generate the image synchronization signal for the image sensor after the second time; and
generate a third instruction information instructing whether or not to generate an image synchronization signal for the image sensor after the first time, based on:
the first instruction information for the first time;
the second instruction information for the first time; and
any one of the first instruction information for the second time, the second instruction information for the second time and the third instruction information instructing whether or not to generate the image synchronization signal for the image sensor after the second time.

16. The capsule endoscope system according to claim 15, wherein the capsule endoscope further comprises:
a communicator configured to perform radio communication with a radio communication device, wherein the communicator is configured to perform at least one of:
transmit at least one of the first data representing the movement of the capsule endoscope at the first time and the first data representing the movement of the capsule endoscope at the second time to the radio communication device for processing by the one or more second processors, and receive the corresponding the first instruction information for the first time and the first instruction information for the second time from the radio communication device; and
transmit the second data to the radio communication device for processing by the one or more second processors, and receive the second instruction information for the first time and the second instruction information for the second time from the communication device.

* * * * *